(12) United States Patent
Dey et al.

(10) Patent No.: US 9,500,622 B2
(45) Date of Patent: Nov. 22, 2016

(54) SPECIFIC ANALYSIS OF KETONE AND ALDEHYDE ANALYTES USING REAGENT COMPOUNDS, LABELING STRATEGIES, AND MASS SPECTROMETRY WORKFLOW

(71) Applicant: DH Technologies Development Pte. Ltd., Singapore (SG)

(72) Inventors: Subhakar Dey, Lexington, MA (US); Sasi Pillal, Littleton, MA (US); Brian L. Williamson, Ashland, MA (US); Subhasish Purkayastha, Acton, MA (US); Michal Weinstock, Newton, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 602 days.

(21) Appl. No.: 13/897,628

(22) Filed: May 20, 2013

(65) Prior Publication Data
US 2014/0004616 A1    Jan. 2, 2014

Related U.S. Application Data

(62) Division of application No. 12/791,435, filed on Jun. 1, 2010, now abandoned.

(60) Provisional application No. 61/182,748, filed on May 31, 2009.

(51) Int. Cl.
*G01N 24/00* (2006.01)
*G01N 27/62* (2006.01)
*G01N 30/72* (2006.01)
(Continued)

(52) U.S. Cl.
CPC ............ *G01N 27/62* (2013.01); *G01N 30/72* (2013.01); *G01N 33/64* (2013.01); *G01N 33/743* (2013.01); *G01N 2030/045* (2013.01); *G01N 2030/884* (2013.01); *H01J 49/00* (2013.01);
(Continued)

(58) Field of Classification Search
CPC ..................... G01N 33/6848; G01N 2458/15; C07C 2101/08; C07C 225/10; C07C 229/36
See application file for complete search history.

(56) References Cited

U.S. PATENT DOCUMENTS 5,880,270 A  3/1999  Berninger et al.
7,309,608 B2  12/2007  Neguyen et al.
(Continued)

FOREIGN PATENT DOCUMENTS

JP  2007-517070 A  6/2007
WO  2004-097372 A2  11/2004
WO  2007-031717 A1  3/2007

OTHER PUBLICATIONS

International Search Report with Notification and Written Opinion for International Application No. PCT/US10/01598, date of mailing Jul. 30, 2010.
(Continued)

*Primary Examiner* — Yelena G Gakh

(57) ABSTRACT

Labeling reagents, sets of labeling reagents, and labeling techniques are provided for the relative quantitation, absolute quantitation, or both, of ketone or aldehyde compounds including, but not limited to, analytes comprising steroids or ketosteroids. The analytes can be medical or pharmaceutical compounds in biological samples. Methods for labeling, analyzing, and quantifying ketone or aldehyde compounds are also disclosed as are methods that also use mass spectrometry.

9 Claims, 19 Drawing Sheets

(51) Int. Cl.
*G01N 33/64* (2006.01)
*G01N 33/74* (2006.01)
*G01N 30/04* (2006.01)
*G01N 30/88* (2006.01)
*H01J 49/00* (2006.01)

(52) U.S. Cl.
CPC ............... *Y10T436/147777* (2015.01); *Y10T 436/200833* (2015.01)

(56) References Cited

U.S. PATENT DOCUMENTS

2005/0148771 A1 7/2005 Dey et al.
2008/0014642 A1 1/2008 Purkayastra

OTHER PUBLICATIONS

European Search Opinion for EP2438448, date of mailing Mar. 26, 2015.

Reagent-114

Reagent-115

Reagent-116

Reagent-117

SPECIFIC ANALYSIS OF KETONE AND ALDEHYDE ANALYTES USING REAGENT COMPOUNDS, LABELING STRATEGIES, AND MASS SPECTROMETRY WORKFLOW

RELATED APPLICATIONS

The present application is a divisional of and claims the benefit of the earlier filing date of U.S. patent application Ser. No. 12/791,435, filed on Jun. 1, 2010, which claims priority to U.S. Provisional Patent Application No. 61/182,748, filed May 31, 2009, both of which are incorporated herein in its entirety by reference.

BACKGROUND

Ketones and aldehydes are polar chemical functionalities having a carbonyl group linked to one or two other carbon atoms. Ketone and aldehydes compounds play an important role in industry, agriculture, and medicine. Ketones and aldehydes are also important agents in human metabolism and biochemistry. Ketosteroids, in particular, are a class of ketone-containing steroid compounds and are uniquely valuable in research and clinical diagnosis because these compounds are critical agents in hormone-regulated biological processes and have strong biological activity at very low concentrations. Many ketosteroids are also potentially valuable pharmaceutical agents and the analysis of their function and metabolism in the body are useful in both medical treatments and diagnostic techniques for the detection of disease.

Analysis and measurement of ketone and aldehyde compounds is challenging because these compounds can be present at low levels in clinical and biological samples such as plasma. Standard chromatographic techniques such as GC-MS methods for analysis after chemical derivatization are available but the chemical derivatization is not specific. See, e.g., Song, J. et al., *Journal of Chromatography B.*, Vol. 791, Issues 1-2, (127-135) 2003. Methods using fluorescence detection are available and some specific immunoassays, including radioimmunoassays (RAs), are available, but these usually do not offer multi-component analysis. The major problems with RAs are lack of specificity and the need to perform a different assay for each steroid.

Examples in the literature of LC/MS strategies exploit derivatization of the analytes, but the ionization efficiency is relatively low and these strategies have failed to achieve the limit of detection required for the assay to be viable in a clinical setting using mass spectrometry and also lack multiplexing capability. Steroid analysis in biological samples is also crucial for the evaluation and clinical detection of various endocrine and metabolic disorders. Clinical laboratories are currently performing radioimmunoassays (RAs) for high throughput screening of steroids.

The above challenges posed by attempting to measure ketone and aldehyde compounds in samples are also magnified by the desire to rapidly screen and/or analyze a large number of biological samples for the specific compounds of interest or a panel of ketone or aldehyde analytes. Although mass spectrometry can provide rapid throughput, ketone and aldehyde steroids are particularly challenging because of interference in the mass measurements by competing compounds and low sample concentrations in the sample medium. In addition, some classes of ketone and aldehyde compounds, and particularly ketosteroids, are not compatible with traditional sample processing conditions often used to prepare samples for mass spectrometric analysis. Ketosteroids are also particularly challenging due to poor ionization efficiency and complex ionization patterns during MS/MS analysis.

Therefore, although techniques for rapid and efficient analysis and quantitation of ketone and aldehyde compounds are highly desirable because of the biological importance of these compounds, the existing techniques are not ideal due to lack of sensitivity, cross-reacting substances, and other challenges inherent in the chemistry of the compounds.

Sensitive, selective, and accurate analysis of ketosteriods can be used for the monitoring of abnormal adrenal functions. The ionization efficiency of native ketosteriods in positive MS/MS can be poor, resulting often times in insufficient limits of detection (LODs), especially when analyzing human samples from infants and children. Derivatization of ketosteroids via their keto functionality to form hydrazines has been used to improve ionization and enhance sensitivity, as described, for example, in Kushnir et al., Performance Characteristics of a Novel Tandem Mass Spectrometry Assay For Serum Testosterone, Clin Chem. 52:1, 120-128, 2006, which is incorporated herein in its entirety by reference.

MRM analysis and MS/MS conditions work well in clean solvent, however, when using complex biological samples, a high background (BKG) noise, often from the same mass Q1/Q3 interfaces, is produced, complicating chromatography and reducing detection limits. A need exits for a method to quantitate ketosteroids and analytes containing a keto or aldehyde functionality.

SUMMARY

The present teachings relates to compounds, methods, and strategies for the analysis of aldehydes and ketones, specifically ketosteroids, in a sample. Labeling compounds are specially designed to derivatize the ketone or aldehyde functionality of an analyte using simple chemistry that can be applied to these compounds in many important biological samples. The derivitization converts a ketone or aldehyde group to an oxime, thereby imparting a more hydrophilic nature to the analyte. Specifically, the ketone or aldehyde functional group is derivatized using aminoxy chemistry to create a labeled analyte that is suitable for ionization and detection by mass spectrometry. In some embodiments, the label reagent is comprised of a mass reporter and an aminoxy group such that the ionized reporter group is detectable. In others, the label comprises a neutral loss group and an aminoxy group such that the charged analyte is detectable by mass spectrometry. In either case, mass analysis of such labeled analytes yield improved detection characteristics, specifically including a large increase in selectivity and a large increase (10-1000 fold) in sensitivity of detection. This strategy also overcomes many of the challenges inherent in measuring or detecting ketone and aldehyde compounds in a sample matrix. The labels and labeling strategy also result in exclusively protonated molecular ions and fragmentation in mass analysis yields a simplified resulting MS spectra.

The methods described herein can measure relative concentration, absolute concentration, or both, and can be applied to one or more steroids in one or more samples. The present methods also include isobaric labeling reagents and methods, as well as mass differential labeling reagents and methods, depending on the selection of isotopic substitution and labeling strategies for the compounds. Isotopically enriched analogues of the labeling regeant can be used and internal standards can be generated for quantitation. United States Patent Application Publication No. US 2005/068446

A1 discloses synthesis of isotopically enriched compounded; mass analysis workflows and strategies are disclosed in U.S. Patent Application Publication No. US 2008/0014642 A1, both of which are incorporated herein in their entireties by reference.

The present teachings provide a method for quantifying ketosteroids and analytes containing keto or aldehyde functionality. In some embodiments, the method can comprise derivatization chemistry and a liquid chromatography/tandem mass spectrometry (LC/MSMS) workflow. The method can comprise using a permanently charged aminoxy reagent which significantly increases the detection limits of ketosteroids. Exemplary aminoxy reagents that can be used include those of formula (I):

Y—(CH$_2$)$n$-ONH$_2$   (I)

wherein n is an integer from 1 to 100 and Y can be any one of these moieties:

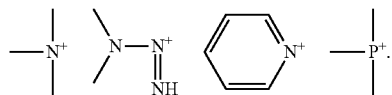

In some embodiments, n is an integer from 2 to 50, or from 2 to 20, or from 2 to 10, or from 2 to 6, or from 3 to 8. In some embodiments, n can be 3 or 4. In some embodiments, Y can be a different charged moiety than any of these four. Y can be a permanently charged moiety, for example, a permanently charged phosphorus-containing or nitrogen-containing moiety. In some embodiments, a kit including one or more of the aminoxy reagents described herein, can be provided.

The method can involve using an MRM workflow for quantitative analysis of ketosteroids. The reagents can be isotope-coded for quantitative analysis of an individual or of a panel of keto compounds. The MS/MS fragmentation at low collision energies is very clean resulting in one predominant signature ion. The signature ion can result from a neutral loss from the aminoxy-derivatized product. The MRM transition can be the mass of the derivatized steroid in Q1 and the mass of the neutral loss fragment in Q3. The present teachings provide a process for significantly reducing background noise via derivatization, resulting in improved sensitivity and targeted selection of Q3 fragments resulting in improved specificity.

BRIEF DESCRIPTIONS OF THE DRAWINGS

FIG. 8A shows a complex fragmentation patterns across the entire spectrum while FIG. 8B shows a simplified spetrum with a strong signal from a derivatized analyte at 117 Da.

DETAILED DESCRIPTION OF INVENTION

Figure 1:
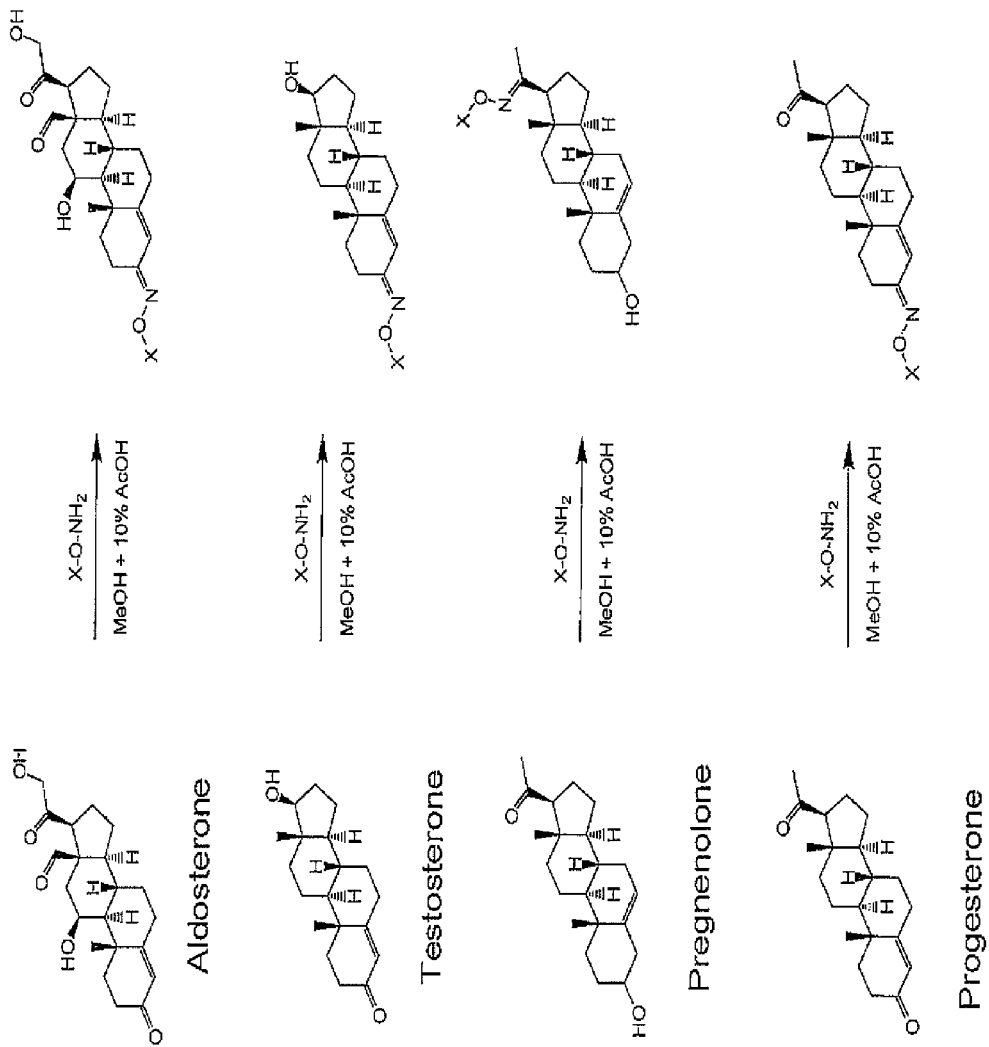
FIG. 1 is a schematic diagram of a one step derivatization reaction of four ketosteroid compounds using labeling reagents disclosed herein.

The ketone and aldehyde compounds used as analytes in the mass spectrometry techniques described herein are found in a variety of sources such as physiological fluid samples, cell or tissue lysate samples, protein samples, cell culture samples, agricultural product samples and essentially any sample where the ketone and aldehyde functionality is present in the analyte. To demonstrate the applicability of the present techniques to ketone and aldehyde compounds, ketosteroids are analyzed and measured in the Examples below. The ketosteroids present a particular challenge due to the low concentrations in the matrix of common clinical samples and the techniques, label reagents and methods applicable thereto are readily applied to ketone or aldehyde compounds.

Moreover, the present teachings can be applied to both natural and synthetic ketone or aldehyde analytes. Ketosteroids including, but not limited to, DHT, testosterone, epitestosterone, desoxymethyltestosterone (DMT), tetrahydrogestrinone (THG), aldosterone, estrone, 4-hydroxyestrone, 2-methoxyestrone, 2-hydroxyestrone, 16-ketoestradiol, 16 alpha-hydroxyestrone, 2-hydroxyestrone-3-methylether, prednisone, prednisolone, pregnenolone, progesterone, DHEA (dehydroepiandrosterone), 17 OH pregnenolone, 17 OH progesterone, 17 OH progesterone, androsterone, epiandrosterone, and D4A (delta 4 androstenedione), and can be analyzed in various embodiments of the present teachings.

The present invention includes reagents and methods using mass differential tags including sets of mass differential labels where one or more labels of the set contains one or more heavy atom isotopes. A set of mass differential labels can also be provided by preparing labels with different overall mass and different primary reporter ion masses or mass balance groups, although not every member of a set of mass differential tags need be isotopically enriched. The present reagents and methods enable analysis of ketone and aldehyde analytes in one or more samples using mass differential labels and parent-daughter ion transition monitoring (PDITM). The present teachings can be used for qualitative and quantitative analysis of such analytes using mass differential tagging reagents and mass spectrometry. The mass differential tags include, but are not limited to, non-isobaric isotope coded reagents and the present invention includes reagents and methods for the absolute quantitation of ketone and aldehyde compounds with or without the use of an isotopically enriched standard compound.

When isotopically enriched isobaric tags are used, sets of isobaric labels may comprise one or more heavy atom isotopes. A set of isobaric labels can have an identical or specifically defined range of aggregate masses but has a primary reporter ion or charged analyte of a different measurable mass. A set of isobaric reagents enables both qualitative and quantitative analysis of ketone and aldehyde analyte compounds using mass spectroscopy. For example, isotopically enriched isobaric tags and parent-daughter ion transition monitoring (PDITM) can measure or detect one or more ketone or aldehyde compounds in a sample such as a specific ketosteroid or group of ketosteroids.

The present invention also includes kits of labeling reagents and sets of labeling reagents for the relative quantitation, absolute quantitation, or both, of ketone compounds in biological samples including labeling reagents can be represented by general formula (II):

$$Z—R_1, \quad (II)$$

and can be provided and/or used in a salt or hydrate form. In general, in formula (II): (a) Z represents a mass reporter group comprised of (i) a substituted or unsubstituted straight, branched or cyclic alkyl; a substituted or unsubstituted aryl; a substituted or unsubstituted hetero aryl; a substituted or unsubstituted amino; or a substituted or unsubstituted thio or (ii) a quarternary nitrogen as an amino group; and (b) $R_1$ represents a substituted or unsubstituted terminal aminoxy having the formula O—NH$_2$.

In various aspects, the present teachings provide labeled analytes, wherein the analyte is comprised at least one ketone group and a label described herein. The labeled ketone compounds can be represented by the general configuration (III): Analyte-Oxime-Label, which may be represented by the formula (III): A-X—R. A represents the compound that contained one or more ketone or aldehyde groups prior to formation of the labeled compound; X represents an oxime group; and R is the label described above.

As noted above, the present teachings are not limited to the analysis of ketosteroids, but can be applied to any compound containing a ketone or aldehyde group by reaction of the ketone or aldehyde group with a label or tag comprised of a terminal aminoxy group, to yield the resulting oxime, and a reporter group or charged analyte susceptible to detection by mass analysis.

In various embodiments, the labeling reagent or labeled analyte compound comprises substituted or unsubstituted terminal aminoxy as follows:

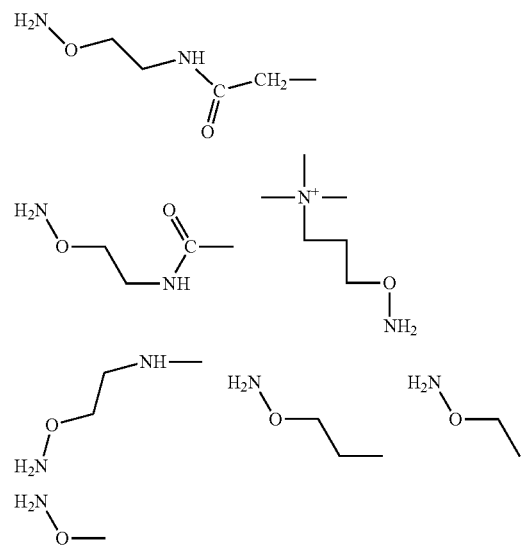

including the following species

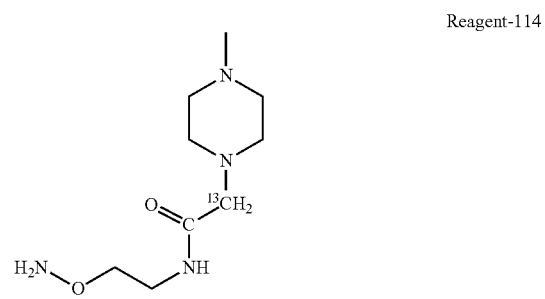

Reagent-114

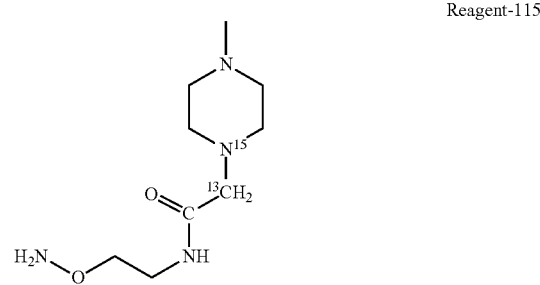

Reagent-115

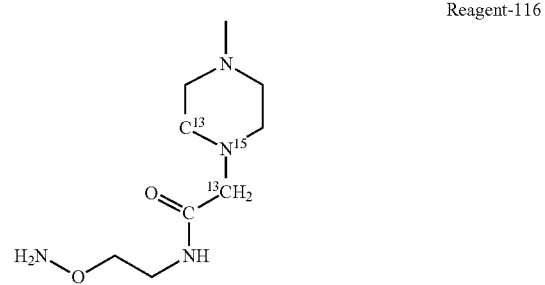

Reagent-116

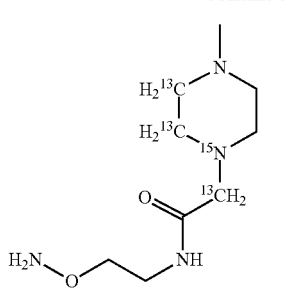

Reagent-117

The present teachings can provide reagents and methods for the analysis of one or more ketone or aldehyde compound in one or more samples using mass differential labels, isobaric labels, or both, and parent-daughter ion transition monitoring (PDITM). The present teachings can provide methods for determining the relative concentration, absolute concentration, or both, of one or more analytes in one or more samples and provide methods whereby the relative concentration, absolute concentration, or both, of multiple analytes in a sample, one or more analytes in multiple samples, or combinations thereof, can be determined in a multiplex fashion using mass differential tagging reagents, isobaric tagging reagents, or both, and mass spectroscopy.

In embodiments comprising sets of isobaric labels, the linker group portion can be referred to as a balance group. For example, a set of four isobaric labels are added to a set of one or more analytes and combined to form a combined sample that is subjected to MS/MS analysis to fragment the labeled ketone or aldehyde compound and produce 4 reporter ions of different mass or charged analytes. The labels can be made isobaric by an appropriate combination of heavy atom substitutions of a reporter group or mass balance group or portion thereof or a mass balance group alone or portion thereof.

The heavy atom isotope distribution may generate a different reporter ion or charged analyte signal in a mass spectrometer. The ion signals produced by labeled components of a mixture (e.g., different analytes, analytes from different samples, standards, etc.) can be deconvoluted by analyzing the reporter ion signal associated with the respective label. Deconvolution can determine the relative and/or absolute amount labeled components in the mixture. These determinations include time course studies, biomarker analysis, multiplex analysis, affinity pull-downs, and multiple control experiments.

"Parent-daughter ion transition monitoring" or "PDITM" is an advantageous method of analysis and workflow status, that refers to a technique whereby the transmitted mass-to-charge (m/z) range of a first mass separator (often referred to as "MS" or the first dimension of mass spectrometry) is specifically selected to transmit a molecular ion (often referred to as "the parent ion" or "the precursor ion") to an ion fragmentor (e.g. a collision cell, photodissociation region, etc.) to produce fragment ions (often referred to as "daughter ions") and the transmitted m/z range of a second mass separator (often referred to as "MS/MS" or the second dimension of mass spectrometry) is selected to transmit one or more daughter ions to a detector which measures the daughter ion signal. This technique offers unique advantages when the detection of daughter ions in the spectrum is focused by "parking" the detector on the expected daughter ion mass. The combination of parent ion and daughter ion masses monitored can be referred to as the "parent-daughter ion transition" monitored. The daughter ion signal at the detector for a given parent ion-daughter ion combination monitored can be referred to as the "parent-daughter ion transition signal".

For example, one embodiment of parent-daughter ion transition monitoring is multiple reaction monitoring (MRM) (also referred to as selective reaction monitoring). In various embodiments of MRM, the monitoring of a given parent-daughter ion transition comprises using as the first mass separator (e.g., a first quadrupole parked on the parent ion m/z of interest) to transmit the parent ion of interest and using the second mass separator (e.g., a second quadrupole parked on the daughter ion m/z of interest) to transmit one or more daughter ions of interest. In various embodiments, a PDITM can be performed by using the first mass separator (e.g., a quadrupole parked on a parent ion m/z of interest) to transmit parent ions and scanning the second mass separator over a m/z range including the m/z value of the one or more daughter ions of interest.

For example, a tandem mass spectrometer (MS/MS) instrument or, more generally, a multidimensional mass spectrometer ($MS_n$) instrument, can be used to perform PDITM, e.g., MRM. Examples of suitable mass analyzer systems include, but are not limited to, those that comprise on or more of a triple quadrupole, a quadrupole-linear ion trap, a quadrupole TOF, and a TOF-TOF.

In various embodiments, for analyzing one or more ketone or aldehyde analyte compounds in one or more samples using labels of the present teachings comprises the steps of: (a) labeling one or more analyte compounds each with a different label from a set of labels of formula (II) providing labeled analyte compounds of formula (III), the labeled analyte compounds each having a mass balance or reporter ion portion; (b) combining at least a portion of each of the labeled analyte compounds to produce a combined sample; (c) subjecting at least a portion of the combined sample to parent-daughter ion transition monitoring; (d) measuring the ion signal of one or more of the transmitted analyte or reporter ions; and (e) determining the concentration of one or more of the labeled ketone or aldehyde analyte compounds based at least on a comparison of the measured ion signal of the corresponding analyte or reporter ion to one or more measured ion signals of a standard compound. Accordingly, in various embodiments, the concentration of multiple analyte compounds in one or more samples can be determined in a multiplex fashion, for example, by combining two or more labeled analyte compounds to produce a combined sample and subjecting the combined sample to PDITM, and monitoring the analyte or reporter ions of two or more of labeled analyte compounds.

In various embodiments, the step of determining the concentration of one or more labeled ketone or aldehyde analyte compounds comprises determining the absolute concentration of one or more of the labeled ketone or aldehyde analyte compounds, determining the relative concentration of one or more of the labeled ketone or analyte compounds, or combinations of both.

A chromatographic column can be used to separate two or more labeled analyte compounds. For example, a first labeled analyte compound found in one or more of the samples is separated by the chromatographic column from a second labeled analyte compound found in one or more of the samples. One or more of the samples of interest can comprise a standard sample containing one or more standard compounds, wherein the measured ion signal of a reporter ion corresponding to a standard compound in the method corresponds to the measured reporter ion signal of one or more labeled standard compounds in the standard sample.

In various embodiments of the present teachings, a concentration curve of a standard compound can be generated by: (a) providing a non-isotopically enriched standard ketone or aldehyde compound having a first concentration; (b) labeling the standard compound with a label from a set of labels wherein the labeled ketone standard compound has a reporter ion portion; (c) loading at least a portion of the labeled standard compound on a chromatographic column; (d) subjecting at least a portion of the eluent from the chromatographic column to parent-daughter ion transition monitoring; (e) measuring the ion signal of the transmitted analyte or reporter ions; (f) repeating steps (a)-(e) for one or more different standard compound concentrations; and (g) generating a concentration curve for the standard compound based at least on the measured ion signal of the transmitted analyte or reporter ions at two or more standard compound concentrations.

As will be readily appreciated in the art, the standard ketone or aldehyde compound can be contained in a standard sample, and a standard sample can contain more than one standard compound. As noted above, the sample can be obtained from research, clinical, agricultural or industrial sources containing a ketone or aldehyde analyte. In various embodiments, a concentration curve of the standard compounds can be generated by: (a) providing a standard sample comprising one or more non-isotopically enriched standard compounds having first concentrations; (b) adding a label to the standard sample to label one or more of the standard compounds in the sample, the labeled standard compounds each having a reporter ion portion; (c) loading at least a portion of the labeled sample on a chromatographic column; (d) subjecting at least a portion of the eluent from the chromatographic column to parent-daughter ion transition monitoring; (e) measuring the ion signal of the transmitted analyte or reporter ions; (f) repeating steps (a)-(e) for one or more different standard samples containing different concentrations of one or more of the standard compounds; and (g) generating a concentration curve for one of more of the standard compounds based at least on the measured ion signal of the transmitted analyte or reporter ions for the corresponding standard compound at two or more standard compound concentrations.

In a preferred embodiment, the step of adding a label to the standard sample to label one or more of the standard compounds in the sample comprises a one step reaction where a terminal aminoxy group forms an oxime with the ketone or aldehyde group of the analyte standard.

The phrases "mass differential labels", "mass differential tags" and "mass differential labeling reagents" are used interchangeably herein. The phrases "set of mass differential labels", "set of mass differential tags" are used interchangeably and refer to, for example, a set of reagents or chemical moieties where the members of the set (i.e., an individual "mass differential label" or "mass differential tag") have substantially similar structural and chemical properties but differ in mass due to differences in heavy isotope enrichment between members of the set. Each member of the set of mass differential tags can produce a different daughter ion signal upon being subjected to ion fragmentation. Ion fragmentation can be, for example, by collisions with an inert gas (e.g., collision induced dissociation (CID), collision a activated dissociation (CAD), etc.), by interaction with photons resulting in dissociation, (e.g., photoinduced dissociation (PID)), by collisions with a surface (e.g., surface induced dissociation (SID)), by interaction with an electron beam resulting in dissociation (e.g., electron induced dissociation (EID), electron capture dissociation (ECD)), thermal/black body infrared radiative dissociation (BIRD), post source decay, or combinations thereof. A daughter ion of a mass differential tag or label that can be used to distinguish between members of the set can be referred to as a reporter ion of the mass differential tag or label.

The phrases "isobaric labels", "isobaric tags" and "isobaric labeling reagents" are used interchangeably. The phrases "set of isobaric labels", "set of isobaric tags" and "set of isobaric labeling reagents" are used interchangeably and refer to, for example, a reagents or chemical moieties where the members of the set (an individual "isobaric label," "isobaric tag," or "isobaric labeling reagent") have the identical mass but where each member of the set can produce a different daughter ion signal upon being subjected to ion fragmentation (e.g., by collision induced dissociation (CID), photoinduced dissociation (PID), etc.). A set of isobaric tags comprises compounds of formula (I) or (II), or a salt or a hydrate form thereof. A daughter ion of an isobaric tag that can be used to distinguish between members of the set can be a reporter ion of the isobaric tag or charged analyte. A set of isobaric tags is used to label ketone or aldehyde compounds and produced labeled compounds that are substantially chromatographically indistinguishable, but which produce signature ions following CID. The masses of the individual members of a set of mass labels can be identical or different. Where the individual isotopic substitutions are the same, the masses can be identical. Differences in selecting individual atoms for the heavy or light element incorporated into a specific label of the set can also yield mass differences based on the specific atomic weights of the isotopically enriched substituents.

As used herein, "isotopically enriched" means that a compound (e.g., labeling reagent) has been enriched synthetically with one or more heavy atom isotopes (e.g. stable isotopes including, but not limited to, Deuterium, $^{13}$C, $^{15}$N, $^{18}$O, $^{37}$Cl, or $^{81}$Br). Because isotopic enrichment is not 100% effective, there can be impurities of the compound that are of lesser states of enrichment and these will have a lower mass. Likewise, because of over-enrichment (undesired enrichment) and because of natural isotopic abundance variations, impurities of greater mass can exist.

As used herein, "natural isotopic abundance" refers to the level (or distribution) of one or more isotopes found in a compound based upon the natural terrestrial prevalence of an isotope or isotopes in nature. For example, a natural compound obtained from living plant matter will typically contain about 0.6% $^{13}$C.

The term "substituted" is intended to describe groups having substituents replacing a hydrogen on one or more atoms, including, but not limited to, carbon, nitrogen, oxygen, etc., of a molecule. Substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkoxyl, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, nitro, trifluoromethyl, cyano, azido, heterocyclyl, alkylaryl, or an aromatic or heteroaromatic group. Accordingly, the phrase "a substituent as described herein" or the like refers to one or more of the above substituents, and combinations thereof.

The term "alkyl" includes saturated aliphatic groups, which includes both "unsubstituted alkyls" and "substituted alkyls", the latter of which refers to alkyl groups having substituents replacing a hydrogen on one or more carbons of the hydrocarbon backbone. The term "alkyl" includes straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), and cycloalkyl substituted alkyl groups. The term "alkyl" also includes the side chains of natural and unnatural amino acids.

An "alkylaryl" or an "aralkyl" group is an alkyl substituted with an aryl (e.g., phenylmethyl (benzyl)).

The term "aryl" includes 5- and 6-membered single-ring aromatic groups, as well as multicyclic aryl groups, e.g. tricyclic, bicyclic, e.g., naphthalene, anthracene, phenanthrene, etc.). The aromatic ring(s) can be substituted at one or more ring positions with such substituents as described above. Aryl groups can also be fused or bridged with, e.g. alicyclic or heterocyclic rings which are not aromatic so as to form, e.g. a polycycle.

The term "alkenyl" includes unsaturated aliphatic groups analogous in length and possible substitution to the alkyls described above, but which contain at least one double bond. For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl includes both "unsubstituted alkenyls" and "substituted alkenyls", the latter of which refers to alkenyl groups having substituents replacing a hydrogen on one or more carbons of the hydrocarbon backbone.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl includes both "unsubstituted alkynyls" and "substituted alkynyls", the latter of which refers to alkynyl groups having substituents replacing a hydrogen on one or more carbons of the hydrocarbon backbone.

The term "acyl" includes compounds and groups which contain the acyl ($CH_3CO-$) or a carbonyl group. The term "substituted acyl" includes acyl groups having substituents replacing a one or more of the hydrogen atoms.

The term "acylamino" includes groups wherein an acyl group is bonded to an amino group. For example, the term includes alkylcarbonylamino, arylcarbonylamino, carbamoyl and ureido groups.

The term "aroyl" includes compounds and groups with an aryl or heteroaromatic group bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g. oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy.

The term "aminoxy" refers to a reactive group on a labeling reagent having a terminal $O-NH_2$ group capable of reacting on a targeted ketone and aldehyde analyte with a ketone or aldehyde moiety to yield an oxime.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group that is bound to at least one alkyl group and at least one aryl group. The term "alkaminoalkyl" refers to an alkyl, alkenyl, or alkynyl group bound to a nitrogen atom that is also bound to an alkyl group.

The term "amide" or "aminocarboxy" includes compounds or groups that contain a nitrogen atom that is bound to the carbon of a carbonyl or a thiocarbonyl group. The term includes "alkaminocarboxy" groups that include alkyl, alkenyl, or alkynyl groups bound to an amino group bound to a carboxy group. It includes arylaminocarboxy groups that include aryl or heteroaryl groups bound to an amino group which is bound to the carbon of a carbonyl or thiocarbonyl group. The terms "alkylaminocarboxy," "alkenylaminocarboxy," "alkynylaminocarboxy," and "arylaminocarboxy" include groups wherein alkyl, alkenyl, alkynyl and aryl groups, respectively, are bound to a nitrogen atom which is in turn bound to the carbon of a carbonyl group.

The term "carbonyl" or "carboxy" includes compounds and groups which contain a carbon connected with a double bond to an oxygen atom, and tautomeric forms thereof. Examples of groups that contain a carbonyl include aldehydes, ketones, carboxylic acids, amides, esters, anhydrides, etc. The term "carboxy group" or "carbonyl group" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl group. For example, the term includes groups such as, for example, aminocarbonyl groups, (wherein a nitrogen atom is bound to the carbon of the carbonyl group, e.g., an amide), aminocarbonyloxy groups, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. groups.

The term "ether" includes compounds or groups that contain an oxygen bonded to two different carbon atoms or heteroatoms. For example, the term includes "alkoxyalkyl"

which refers to an alkyl, alkenyl, or alkynyl group covalently bonded to an oxygen atom that is covalently bonded to another alkyl group.

The term "ester" includes compounds and groups that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH or —O$^-$.

The term "heteroatom" includes atoms of any element other than carbon or hydrogen. Preferred heteroatoms are nitrogen, and oxygen. The term "heterocycle" or "heterocyclic" includes saturated, unsaturated, aromatic ("heteroaryls" or "heteroaromatic") and polycyclic rings which contain one or more heteroatoms. The heterocyclic may be substituted or unsubstituted. Examples of heterocyclics include, for example, benzodioxazole, benzofuran, benzoimidazole, benzothiazole, benzothiophene, benzoxazole, chromene, deazapurine, furan, indole, indolizine, imidazole, isoxazole, isoindole, isoquinoline, isothiaozole, methylenedioxyphenyl, napthridine, oxazole, purine, pyran, pyrazine, pyrazole, pyridazine, pyridine, pyrimidine, pyrrole, quinoline, tetrazole, thiazole, thiophene, and triazole. Other heterocycles include morpholino, piprazine, piperidine, thiomorpholino, and thioazolidine.

The terms "polycyclic ring" and "polycyclic ring structure" include groups with two or more rings (e.g., cycloalkyls, cycloalkenyls, cycloalkynyls, aryls and/or heterocyclyls) in which two or more carbons are common to two adjoining rings, e.g. the rings are "fused rings". Rings that are joined through non-adjacent atoms are termed "bridged" rings. Each of the rings of the polycyclic ring can be substituted with such substituents as described above.

As used herein, the term "salt form" includes a salt of a compound or a mixture of salts of a compound. In addition, zwitterionic forms of a compound are also included in the term "salt form." Salts of compounds having an amine, or other basic group can be obtained, for example, by reaction with a suitable organic or inorganic acid, such as hydrogen chloride, hydrogen bromide, acetic acid, perchloric acid and the like. Compounds with a quaternary ammonium group may also contain a counteranion such as chloride, bromide, iodide, acetate, perchlorate and the like. Salts of compounds having a carboxylic acid, or other acidic functional group, can be prepared by reacting the compound with a suitable base, for example, a hydroxide base. Accordingly, salts of acidic functional groups may have a countercation, such as sodium, potassium, magnesium, calcium, etc.

As used herein, "hydrate form" refers to any hydration state of a compound or a mixture or more than one hydration state of a compound. For example, a labeling reagent discussed herein can be a hemihydrate, a monohydrate, a dihydrate, etc. Moreover, a sample of a labeling reagent described herein can comprise monohydrate, dihydrate and hemihydrate forms.

Labeling Reagents

Described herein are sets of mass differential labels of general formula (I) or (II) as described above. In various embodiments, provided are sets of isobaric labels of general formula (I) or (II) in their unsalted and/or unhydrated form. In various embodiments, the masses of the labels differ by less than about 0.05 amu in the unsalted and/or unhydrated form. The sets of labels provided comprise two or more compounds of the general formula (I) or (II) wherein one or more of the compounds in the set of labels contains one or more heavy atom isotopes. In various embodiments, the heavy atom isotopes are each independently $^{13}$C, $^{15}$N, $^{18}$O, $^{33}$S, or $^{34}$S.

The compounds of formula (I) or (II) can be provided in a wide variety of salt and hydrate forms including, but not limited to, a mono-TFA salt, a mono HCl salt, a bis-HCl salt, or a bis-TFA salt, or a hydrate thereof. Variation on formula (I) or (II) are disclosed in WO2005/068446 which is specifically incorporated by reference and are generally referred to as iTRAQ reagents.

In various embodiments, the one or more of the compounds of the set of labels is isotopically enriched with two or more heavy atoms; three or more heavy atoms; and/or with four or more heavy atoms. In various embodiments, a set of labels of formula incorporated heavy atom isotope such that the isotopes are present in at least 80 percent isotopic purity, at least 93 percent isotopic purity, and/or at least 96 percent isotopic purity.

The reporter group may be comprised of one or more 5, 6 or 7-membered heterocyclic rings as described in U.S. Patent Application Publication No. US 2008/0014642 A1 which is specifically incorporated herein in its entirety by reference.

A set of four isobaric tags of a set of isobaric tags may comprise a reporter portion and a balance group portion. In various embodiments, one or more analytes from one or more samples are labeled with an isobaric tag, the labeled analytes mass filtered (e.g., with a TOF MS, a RF Multipole MS, a ion mobility MS, etc.) and subjected to fragmentation (e.g., collision induced dissociation (CID), photodissociation, etc.) to produce a reporter ion that can be detected by mass spectrometry.

Reporter Groups & Ions

The reporter group portion of an isobaric tag of the present teachings can be a group that produces a reporter ion from a labeled analyte when the labeled analyte is subjected to fragmentation; this reporter ion having a substantially consistent mass and/or mass-to-charge ratio that can be determined by mass spectrometry. A charged analyte can also function as a reporter group for detection by mass analysis. Thus, the reporter group may be a component of the label reagent or may be the analyte itself. In some embodiments, the reporter ions of different isobaric reagent tags in set of isobaric tags have different masses and/or mass-to-charge ratios (m/z). Different reporter groups, analytes, standards or ions can comprise one or more heavy atom isotopes to achieve the differences in mass or m/z between different tags. For example, heavy atom isotopes of carbon ($^{12}$C, $^{13}$C, and $^{14}$C), nitrogen ($^{14}$N and $^{15}$N), oxygen ($^{16}$O and $^{18}$O), sulfur ($^{32}$S, $^{33}$S, and $^{34}$S), and/or hydrogen (hydrogen, deuterium and tritium) can be used in the preparation of a diverse group of reporter groups and ions.

Ions of the labeled analyte are fragmented to thereby produce detectable daughter fragment ions. The detected daughter ion signal can be used, e.g., to identify the sample from which an analyte originated. The detected daughter ion signal can be used, e.g., to determine the relative or absolute amount of analyte in the sample or samples. The absolute amount is often expressed as a concentration and/or quantity. For example, the amount of a labeled analyte in a sample can be determined by comparing the daughter ion signal to those of other daughter ions, a calibration standard, and the like. In some embodiments, information such as the amount of one or more analytes in a particular sample can be associated with the reporter ion that corresponds to the reporter group of the isobaric tag used to label each particular sample. The identity of the analyte or analytes can be correlated with information pertaining to the different reporter or daughter ions to thereby facilitate the determination of the identity and amount of each labeled analyte in one or a plurality of samples.

When the labeling reagent is comprised of a different reporter group, the reporter group can comprise a fixed charge or can be capable of becoming ionized. In various embodiments, use can be made of a reporter group having a fixed charge or being capable of being ionized, to isolate and/or use the isobaric tag to label an analyte in a salt, in a mixture of salts), in zwitterionic form, or a combination thereof. Ionization of the reporter group facilitates its determination in a mass spectrometer. When ionized, the reporter group can comprise one or more net positive or negative charges. Thus, the reporter group can comprise one or more acidic groups or basic groups since various embodiments of such groups can be easily ionized in a mass spectrometer. For example, the reporter group can comprise one or more basic nitrogen atoms (positive charge) or one or more ionizable acidic groups such as a carboxylic acid group, sulfonic acid group or phosphoric acid group (negative charge). Examples of reporter groups comprising a basic nitrogen include, but are not limited to, substituted or unsubstituted, morpholines, piperidines or piperazines.

Accordingly, the reporter group can be selected to produce a reporter ion that does not substantially sub-fragment under conditions typical for the analysis of an analyte. The reporter ion does not substantially sub-fragment under conditions of dissociative energy applied to cause fragmentation of the bond between the nitrogen of the alkyl amide of the reporter group and the balance group. A reporter that does not "substantially sub-fragment," means that fragments of the reporter ion are difficult or impossible to detect above background noise when applied to the successful analysis of the analyte of interest.

The mass of a reporter ion can be selected to be different as compared with the mass of the analyte of interest and/or any of the expected fragments of the analyte. For example, particularly where proteins or peptides are the analytes, the reporter ion mass can be chosen to be different as compared with any naturally occurring amino acid or peptide, or expected fragments thereof.

In specific embodiments described herein, the parent ion is a ketosteroid labeled with an isobaric tag and the daughter ion is a reporter ion of the isobaric tag. Accordingly, the ion signal of a reporter ion that is measured at a detector for a given isobarically labeled steroid parent ion can be referred to as a "labeled ketosteroid-reporter ion transition signal". Similarly, the ion signal of a reporter ion that is measured at a detector for a given isobarically labeled standard compound can be referred to as a "labeled standard-reporter ion transition signal". Also, where the label is comprised of a mass balance group, the ion signal of a charged analyte can be characterized as a "labeled analyte ion transition signal."

Balance Groups

According to various embodiments, isotopes can be used as balance groups or balance moieties, for example, isotopes of hydrogen, carbon, nitrogen, oxygen, sulfur, chlorine, bromine, and the like. Exemplary balance groups or moieties can also include those described, for example, in U.S. Patent Application Publications Nos. US 2004/0219685 A1, published Nov. 4, 2004, US 2004/0219686 A1, published Nov. 4, 2004, US 2004/0220412 A1, published Nov. 4, 2004, and US 2010/0112708 A1, published May 6, 2010, all of which are incorporated herein in their entireties by reference.

Applications

The ketone or aldehyde analyte compounds that can be analyzed can come from a wide variety of source types such as, for example, physiological fluid samples, cell or tissue lysate samples, protein samples, cell culture samples, fermentation broth media samples, agricultural product samples, animal product samples, animal feed samples, samples of food or beverage for human consumption, combinations thereof, and the like. The samples can be from different sources, conditions, or both; for example, control vs. experimental, samples from different points in time (e.g. to form a sequence), disease vs. normal, experimental vs. disease, contaminated vs. non-contaminated, etc. Examples of physiological fluids, include, but are not limited to, blood, serum, plasma, sweat, tears, urine, peritoneal fluid, lymph, vaginal secretion, semen, spinal fluid, ascetic fluid, saliva, sputum, breast exudates, and combinations thereof.

Methods of Labeling

In various aspects, the present teachings provide methods for labeling a keto analyte to form a labeled analyte compound. In various embodiments, the methods comprise reacting a labeling compound of the general formula (I) or (II) with a ketone-containing compound. Specifically, ketosteroids were derivatized with the labeling reagent of formula I and specifically labeled as in FIG. 1 in 10% acetic acid in MeOH for 30 minutes at room temperature.

The present teachings can be applied to both naturally produced as well as synthetic ketosteroids. Examples of ketosteroids, including, but not limited to, any steroid, metabolite or derivation thereof containing a ketone graph, such as the keto-forms of cortisol, 11-desoxycortisol (compound S), corticosterone, DHT, testosterone, epitestosterone, desoxymethyltestosterone (DMT), tetrahydrogestrinone (THG), estrone, 4-hydroxyestrone, 2-methoxyestrone, 2-hydroxyestrone, 16-ketoestradiol, 16 alpha-hydroxyestrone, 2-hydroxyestrone-3-methylether, prednisone, prednisolone, pregnenolone, progesterone, DHEA (dehydroepiandrosterone), 17 OH pregnenolone, 17 OH progesterone, 17 OH progesterone, androsterone, epiandrosterone, and D4A (delta 4 androstenedione).

Referring to the Examples, FIGS. and Tables below, an example of labeling ketosteroid analytes such as testosterone, aldosterone, pregnenolone, and progesterone, with labeling reagents is shown. In these reactions, the aminoxy moiety reacts with the ketone or aldehyde on the steroid to form anoxime group on the labeled compound to yield a labeled analyte.

Methods of Analysis

As described herein, methods for determining the concentration of one or more ketone or aldehyde compounds in two or more samples are provided by adding a different label to each sample, combining the differentially labeled samples and using PDITM to determine a concentration of one or more of the analyte compounds in the samples. One of the samples may comprise a standard sample, such as a control sample, a reference sample, a sample with a compound of known concentration, etc. The methods can thus provide an analysis of multiple compounds from multiple samples.

Certain methods comprise the steps of labeling one or more ketone or aldehyde compounds, in two or more samples of interest by adding to each sample of interest a different tag from a set of tags to form a panel of labeled ketone or aldehyde analyte compounds. Each tag from the set of tags may comprise a reporter ion portion as described herein or the ionized analyte may function as the reporter group. One or more of the labeled ketone or aldehyde analyte compounds may be differentially labeled with respect to the sample from which each analyte was obtained or in which it is contained. The step of adding a label to a ketone or aldehyde compound may comprise a one step reaction where a first portion of the label is comprised of the formula Z—$R_1$, wherein $R_1$ is a terminal aminoxy group and Z is a mass reporter or mass balance group.

A portion of each of the samples may be combined to produce a combined sample and a portion thereof analyzed by parent-daughter ion transition monitoring and measuring the ion signal of one or more of the transmitted ions. The transmitted parent ion m/z range includes a m/z value of the labeled analyte compound and the transmitted daughter ion m/z range includes a m/z value of a reporter ion derived to the tag of the labeled analyte compound or is the ionized analyte itself. The concentration of one or more of the labeled analyte compounds can then be determined based at least on a comparison of the measured ion signal of the corresponding transmitter reporter or analyte ions to one or more measured ion signals of a standard compound. The ion signal(s) can, for example, be based on the intensity (average, mean, maximum, etc.) of the ion peak, an area of the ion peak, or a combination thereof. One or more of the two or more samples of interest can be a standard sample containing one or more the standard compounds.

The concentration of a ketone or aldehyde compound is determined by comparing the measured ion signal of the corresponding labeled aldehyde ketone analyte compound-reporter ion transition signal to one or more of:

(i) a concentration curve for a standard compound-reporter or analyte ion transition; and (ii) a standard compound-reporter ion transition signal for a standard compound in the combined sample with the labeled ketone or aldehyde analyte compound.

PDITM can be performed on a mass analyzer system comprising a first mass separator, and ion fragmentor and a second mass separator. The transmitted parent ion m/z range of a PDITM scan (selected by the first mass separator) is selected to include a m/z value of one or more of the labeled analyte compounds and the transmitted daughter ion m/z range of a PDITM scan (selected by the second mass separator) is selected to include a m/z value one or more of the reporter ions corresponding to the tag of the transmitted labeled analyte compound.

In some embodiments, parent daughter ion transition monitoring (PDITM) of the labeled analytes is performed using a triple quadrupole MS platform. More details about PDITM and its use are described in U.S. Patent Application Publication No. US 2006/0183238 A1, which is incorporated herein in its entirety by reference. In some embodiments, the aminoxy MS tagging reagent undergoes neutral loss during MSMS and leaves a reporter ion that is a charged analyte species. In some embodiments, the aminoxy MS tagging reagent forms a reporter ion that is a tag fragment during MSMS.

The tags added to the two or more samples are selected from a set of tags within one experimental measurement: (i) multiple aldehyde or ketone analyte compounds from different samples (e.g., a control, treated, time sequence of samples) can be compared and/or quantified; (ii) multiple concentration measurements can be determined on the same ketone or aldehyde compound from different samples; and (iii) different isolates of a clinical sample can be evaluated against a baseline sample; etc.

The step of subjecting at least a portion of the combined sample to PDITM comprises loading the portion of the combined sample on a chromatographic column (e.g., a LC column, a gas chromatography (GC) column, or combinations thereof), subjecting at least a portion of the eluent from the chromatographic column to parent-daughter ion transition monitoring and measuring the ion signal of one or more of the transmitted reporter ions.

The chromatographic column is used to separate two or more labeled analyte compounds, which differ in the analyte portion of the labeled compound. For example, a first labeled aldehyde or ketone compound found in one or more of the samples is separated by the chromatographic column from a second labeled ketone analyte compound found in one or more of the samples. Two or more different labeled analyte compounds are separated such that the different compounds do not substantially co-elute. Such chromatographic separation can further facilitate the analysis of multiple compounds in multiple samples by, for example, providing chromatographic retention time information on a compound.

The one or more measured ion signals of a standard compound used in the step of determining the concentration of one or more of the labeled analyte compounds can be provided in many ways. In various embodiments, one or more non-isotopically enriched standard compounds are labeled with a tag and at least a portion of one or more of the one or more labeled standard compounds is combined with at least a portion of each of the labeled analyte compounds to produce a combined sample; followed by subjecting at least a portion of this combined sample to PDITM and measuring the ion signal of one or more of the transmitted reporter ions.

A tag from the set of tags is added to one or more standard samples to provide one or more labeled standard samples, each standard sample containing one or more non-isotopically enriched standard compounds that are labeled by the tag, the tag added to the one or more standard samples being different from the tags added to the samples of interest. At least a portion of one or more of the one or more labeled standard samples is combined with at least a portion of each of the samples of interest to produce a combined sample; followed by subjecting at least a portion of this combined sample to PDITM and measuring the ion signal of one or more of the transmitted reporter ions.

The measured ion signals of one or more of the reporters or analyte ions corresponding to one or more of the one or more labeled standard compounds in the combined sample can then be used in determining the concentration of one or more of the labeled analyte compounds and can be used to generate a concentration curve by plotting several values for standard compounds. Accordingly, determining the concentration of a labeled analyte compound is based at least on a comparison of the measured ion signal of the corresponding reporter or analyte ions to the measured ion signal of one or more reporter or analyte ions corresponding to one or more of the one or more labeled standard compounds in the combined sample. The step of subjecting at least a portion of this combined sample to PDITM can comprise, e.g., a direct introduction into a mass analyzer system; first loading at least a portion of this combined sample on a chromatographic column followed by subjecting at least a portion of the eluent from the chromatographic column to PDITM and measuring the ion signal of one or more of the transmitted reporter ions.

As disclosed herein, PDITM on a standard compound can be performed on a mass analyzer system comprising a first mass separator, and ion fragmentor and a second mass separator. The transmitted parent ion m/z range of a PDITM scan (selected by the first mass separator) is selected to include a m/z value of one or more of the labeled standard compounds and the transmitted daughter ion m/z range of a PDITM scan (selected by the second mass separator) is selected to include a m/z value one or more of the reporter or analyte ions corresponding to the transmitted standard compound.

Determining the concentration of one or more of the labeled analyte compounds can be based on both: (i) a comparison of the measured ion signal of the corresponding reporter or analyte ion to the measured ion signal of one or more reporter or analyte ions corresponding to one or more concentration curves of one or more standard compounds, and (ii) a comparison of the measured ion signal of the corresponding reporter ion to the measured ion signal of one or more reporter ions corresponding to one or more labeled standard compounds combined with the labeled ketone or aldehyde analyte. A non-isotopically enriched standard compound is provided having a first concentration and labeled with a tag from the set of tags is combined with at least a portion of each of the labeled samples to produce a combined sample, and this combined sample can then be further analyzed as described herein.

The present disclosure provides methods for determining the concentration of one or more ketone or aldehyde analyte compounds in one or more samples. The methods comprise the steps of labeling one or more ketone or aldehyde compounds each with a different tag from a set of tags of formula (I) or (II), wherein R is comprised of a terminal aminoxy group and Z is comprised of a mass reporter group or a mass balance group. Where the Z group from each tag from the set of tags comprises a reporter ion portion, at least a portion of each of the labeled analyte compound can be combined to produce a combined sample and at least a portion of the combined sample can be subjected to parent-daughter ion transition monitoring (where the transmitted parent ion m/z range includes a m/z value of the labeled analyte compound and the transmitted daughter ion m/z range includes a m/z value of a reporter ion corresponding to the tag of the labeled analyte compound) and measuring the ion signal of one or more of the transmitted reporter ions; then determining the concentration of one or more of the labeled analyte compounds based at least on a comparison of the measured ion signal of the corresponding reporter ion to one or more measured ion signals of a standard compound. The ion signal(s) can, for example, be based on the intensity (average, mean, maximum, etc.) of the ion peak, an area of the ion peak, or a combination thereof.

PDITM can be performed on any suitable mass analyzer known in the art, including a mass analyzer system comprising a first mass separator, and ion fragmentor and a second mass separator. The transmitted parent ion m/z range of a PDITM scan (selected by the first mass separator) is selected to include a m/z value of one or more of the labeled analyte compounds and the transmitted daughter ion m/z range of a PDITM scan (selected by the second mass separator) is selected to include a m/z value one or more of the reporter ions corresponding to the tag of the transmitted labeled analyte compound.

The one or more ketone or aldehyde compound samples are labeled with one or more of tags selected from a set of mass differential tags so that within the same experimental measurement: (i) multiple ketone or aldehyde containing compounds from different samples (e.g., a control, treated) can be compared and/or quantified; (ii) multiple concentration measurements can be determined on the same ketone or aldehyde compound from the same sample; and (iii) different isolates of a clinical sample can be evaluated against a baseline sample.

The step of subjecting at least a portion of the combined sample to PDITM comprises introducing the combined sample directly into a mass analyzer system, e.g., by introduction of the combined sample in a suitable solution using an electrospray ionization (ESI) ion source.

The measured ion signals of one or more of the reporters ions corresponding to one or more of the one or more labeled standard compounds in the combined sample determines the concentration of one or more of the labeled analyte compounds. As noted above, where the label is comprised of a mass balance group and the aminoxy group, the charged analyte acts as the reporter group. Determining the concentration of a labeled analyte compound is based at least on a comparison of the measured ion signal of the corresponding reporter or analyte ion to the measured ion signal of one or more reporter or analyte ions corresponding to one or more of the one or more labeled standard compounds in the combined sample. The step of subjecting at least a portion of this combined sample to PDITM can comprise, e.g., a direct introduction into a mass analyzer system; first loading at least a portion of this combined sample on a chromatographic column followed by subjecting at least a portion of the eluent from the chromatographic column to PDITM and measuring the ion signal of one or more of the transmitted reporter or analyte ions; or combinations thereof.

Determining the concentration of one or more of the labeled analyte compounds includes a comparison of the measured ion signal of the corresponding analyte or reporter ion to the measured ion signal of one or more reporter ions corresponding to one or more concentration curves of one or more standard compounds. A non-isotopically enriched standard compound is provided having a first concentration and labeled with a tag from a set of tags. A portion of the labeled standard compound is subjected to parent-daughter ion transition monitoring (where the transmitted parent ion m/z range includes a m/z value of the labeled standard compound and the transmitted daughter ion m/z range includes a m/z value of a reporter or analyte ion corresponding to the tag of the labeled standard compound) and the ion signal of the reporter or analyte ion is measured. The steps of labeling and the steps of PDITM and measuring the ion signal of the transmitted reporter or analyte ions are repeated for at least one more standard compound concentration different from the first concentration to generate a concentration curve for the standard compound.

The present teachings provide a method for quantifying ketosteroids and analytes containing keto or aldehyde functionality. In some embodiments, the method can comprise derivatization chemistry and a liquid chromatography/tandem mass spectrometry (LC/MSMS) workflow. The method can comprise using a permanently charged aminoxy reagent, which significantly increases the detection limits of ketosteroids. Exemplary aminoxy reagents that can be used include those of formula (I):

Wherein Y can be any one of there moieties:

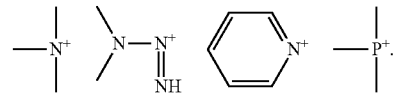

In some embodiments, n is an integer from 2 to 50, or from 2 to 20, or from 2 to 10, or from 2 to 6, or from 3 to 8. In some embodiments, n can be 3 or 4. In some embodiments, Y can be a different charged moiety than any of these four. Y can be a permanently charged moiety, for example, a permanently charged phosphorus-containing or nitrogen-containing moiety. In some embodiments, Y can be a different charged moiety than those shown above. In some embodiments, a kit including one or more of the aminoxy reagents described herein can be provided, for example, comprising one or more permanently charged aminoxy compounds of formula (I).

The method can involve using an MRM workflow for quantitative analysis of ketosteroids. The reagents can be isotope-coded for quantitative analysis of an individual or of a panel of keto compounds. The MS/MS fragmentation at low collision energies is very clean resulting in one predominant signature ion. The signature ion can result from a neutral loss from the aminoxy derivatized product. The MRM transition can be the mass of the derivatized steroid in Q1 and the mass of the neutral loss fragment in Q3. The present teachings provide a process for significantly reducing background noise via derivatization, resulting in improved sensitivity and targeted selection of Q3 fragments resulting in improved specificity.

According to various embodiments, the present teachings provide a method that reduces or eliminates background noise without the problems associated with multistep cleanup of a biological sample and chromatographic separation. In some embodiments, the method eliminates background noise by utilizing a derivatization chemistry of ketosteroids with permanently charged Aminoxy reagents (QAO) and targeted fragmentation that includes both the reagent and the backbone of the derivatized steroid. The derivatization with a readily ionized/ionizable molecule results in better ionization efficiency in ESI MS/MS which increases sensitivity to the analyte. When the fragment ion that is the Q3 signature ion is selected to include structural fragments with an attached derivatization reagent, or a part of the reagent, both the sensitivity and selectivity can be enhanced. The chances that a compound with exactly the same Q1/Q3 transition would be detected and create background noise interference are very low. The only possibility for a similar Q1/Q3 MRM transition would be the existance of an isobaric ketosteroid in the biological sample. The isobaric ketosteroid would have to share the same fragmentation pattern with the analyte in order to appear as interference. In such a rare scenario, the isobaric ketosteroid can be chromatographically separated from the analyte.

According to various embodiments, an added advantage of the reagent design is that on MSMS fragmentation the reagent generates a fragment ion, that is, a Q3 signature ion, with a charge on the dervatized analyte, making it amenable to MS3 analysis. In some embodiments, the method can be implemented on classes of molecules with keto- or aldehyde functionality, the detection of which can benefit from derivatization for ultra high sensitivity analysis by MS/MS.

The present teachings provide a highly sensitive and specific analysis of ketosteroids and classes of molecules containing a keto functionality. The present teachings provide higher signal to noise ratios with very low background noise in MS/MS.

Kits

The present invention provides kits for the analysis of ketone or aldehyde analyte compounds. The kit comprises one or more labels, including a set of two or more isobaric tags and one or more reagents, containers, enzymes, buffers and/or instructions for use. Kits of the present teachings comprise one or more sets of supports, each support comprising a different isobaric labeling compound cleavably linked to the support through a cleavable linker. Examples of cleavable linkages include, but are not limited to, a chemically or photolytically cleavable linker. The supports can be reacted with different samples thereby labeling the analytes of a sample with the isobaric tag associated with the respective support. Ketone analytes from different samples can be contacted with different supports and thus labeled with different reporter/linker combinations.

According to various embodiments, the kit can comprise a plurality of different aminoxy tagging reagents, for example, a set of reagents as described herein. The kit can be configured to analyze a plurality of different keto or aldehyde analytes, for example, a plurality of different steroids or ketosteroids, and the labeling can comprise labeling each with a plurality of different respective tagging reagents, for example, a different tagging reagent for each different type of analyte. The analytes to be analyzed and for which a kit can be configured to detect, can comprise keto or aldehyde compounds, for example, steroids or ketosteroids. According to various embodiments of the present teachings, a kit is provided that comprises one or more aminoxy MS tagging reagents for tagging one or more ketone or aldehyde analytes. The aminoxy MS tagging reagent can comprise a compound having one of the structures described herein.

The kit can comprise a standard comprising a known ketone or aldehyde compound, a known steroid, a known ketosteroid, or a combination thereof. The standard can comprise a known concentration of a known compound. In some embodiments, the aminoxy MS tagging reagent included in the kit can comprise one or more isobaric tags from a set of isobaric tags. In some embodiments, the kit can comprise a plurality of different isobaric tags from a set of isobaric tags. In some embodiments, the aminoxy MS tagging reagent included in the kit can comprise one or more permanently charged aminoxy reagents from a set of permanently charged aminoxy reagents. In some embodiments, the kit can comprise a plurality of different permanently charged aminoxy reagent tagss from a set of permanently charged aminoxy reagent tags.

The kit can also comprise instructions for labeling the analyte, for example, paper instructions or instructions formatted in an electronic file, for example, on a compact disk. The instructions can be for carrying out an assay. In some embodiments, the kit can comprise a homogeneous assay in a single container, to which only a sample need be added. Other components of the kit can include buffers, other reagents, one or more standards, a mixing container, one or more liquid chromatography columns, and the like.

In some embodiments, a ketosteroid analysis kit is provided that enables highly sensitive quantitation of ketosteroids from complex biological matrices, for example, detection in the range of low pg/mL concentrations.

Mass Analyzers

A wide variety of mass analyzer systems can be used in the present teachings to perform PDITM. Suitable mass analyzer systems include two mass separators with an ion fragmentor disposed in the ion flight path between the two mass separators. Examples of suitable mass separators include, but are not limited to, quadrupoles, RF multipoles, ion traps, time-of-flight (TOF), and TOF in conjunction with a timed ion selector. Suitable ion fragmentors include, but are not limited to, those operating on the principles of: collision induced dissociation (CID, also referred to as collisionally assisted dissociation (CAD)), photoinduced dissociation (PID), surface induced dissociation (SID), post source decay, by interaction with an electron beam (e.g., electron induced dissociation (EID), electron capture dissociation (ECD)), interaction with thermal radiation (e.g., thermal/black body infrared radiative dissociation (BIRD)), post source decay, or combinations thereof.

Examples of suitable mass spectrometry systems for the mass analyzer include, but are not limited to, those which comprise one or more of a triple quadrupole, a quadrupole-linear ion trap (e.g., 4000 Q TRAP® LC/MS/MS System, Q TRAP® LC/MS/MS System), a quadrupole TOF (e.g., QSTAR® LC/MS/MS System), and a TOF-TOF.

In various embodiments, the mass analyzer system comprises a MALDI ion source. In various embodiments, at least a portion of the combined sample is mixed with a MALDI matrix material and subjected to parent-daughter ion transition monitoring using a mass analyzer with a MALDI ionization source. In various embodiments, at least a portion of the combined sample loaded on chromatographic column and at least a portion of the eluent mixed with a MALDI matrix material and subjected to parent-daughter ion transition monitoring using a mass analyzer with a MALDI ionization source.

The mass spectrometer system can comprise a triple quadrupole mass spectrometer for selecting a parent ion and detecting fragment daughter ions thereof. In this embodiment, the first quadrupole selects the parent ion. The second quadrupole is maintained at a sufficiently high pressure and voltage so that multiple low energy collisions occur causing some of the parent ions to fragment. The third quadrupole is selected to transmit the selected daughter ion to a detector. In various embodiments, a triple quadrupole mass spectrometer can include an ion trap disposed between the ion source and the triple quadrupoles. The ion trap can be set to collect ions (e.g., all ions, ions with specific m/z ranges, etc.) and after a fill time, transmit the selected ions to the first quadrupole by pulsing an end electrode to permit the selected ions to exit the ion trap. Desired fill times can be determined, e.g., based on the number of ions, charge density within the ion trap, the time between elution of different signature peptides, duty cycle, decay rates of excited state species or multiply charged ions, or combinations thereof.

One or more of the quadrupoles in a triple quadrupole mass spectrometer can be configurable as a linear ion trap (e.g., by the addition of end electrodes to provide a substantially elongate cylindrical trapping volume within the quadrupole). In various embodiments, the first quadrupole selects the parent ion. The second quadrupole is maintained at a sufficiently high collision gas pressure and voltage so that multiple low energy collisions occur causing some of the parent ions to fragment. The third quadrupole is selected to trap fragment ions and, after a fill time, transmit the selected daughter ion to a detector by pulsing an end electrode to permit the selected daughter ion to exit the ion trap. Desired fill times can be determined, e.g., based on the number of fragment ions, charge density within the ion trap, the time between elution of different signature peptides, duty cycle, decay rates of excited state species or multiply charged ions, or combinations thereof.

The mass spectrometer system can comprise two quadrupole mass separators and a TOF mass spectrometer for selecting a parent ion and detecting fragment daughter ions thereof. In various embodiments, the first quadrupole selects the parent ion. The second quadrupole is maintained at a sufficiently high pressure and voltage so that multiple low energy collisions occur causing some of the ions to fragment, and the TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof.

The mass spectrometer system can comprise two TOF mass analyzers and an ion fragmentor (such as, for example, CID or SID). In various embodiments, the first TOF selects the parent ion (e.g., by deflecting ions that appear outside the time window of the selected parent ions away from the fragmentor) for introduction in the ion fragmentor and the second TOF mass spectrometer selects the daughter ions for detection, e.g., by monitoring the ions across a mass range which encompasses the daughter ions of interest and extracted ion chromatograms generated, by deflecting ions that appear outside of the time window of the selected daughter ions away from the detector, by time gating the detector to the arrival time window of the selected daughter ions, or combinations thereof. The TOF analyzers can be linear or reflecting analyzers.

The mass spectrometer system can comprise a tandem MS-MS instrument comprising a first field-free drift region having a timed ion selector to select a parent ion of interest, a fragmentation chamber (or ion fragmentor) to produce daughter ions, and a mass separator to transmit selected daughter ions for detection. In various embodiments, the timed ion selector comprises a pulsed ion deflector. In various embodiments, the ion deflector can be used as a pulsed ion deflector. The mass separator can include an ion reflector. In various embodiments, the fragmentation chamber is a collision cell designed to cause fragmentation of ions and to delay extraction. In various embodiments, the fragmentation chamber can also serve as a delayed extraction ion source for the analysis of the fragment ions by time-of-flight mass spectrometry.

In some embodiments, ionization can be used to produce structurally specific fragment ions and Q3 MRM ions. The labeling reagent can be wholly or partly contained in the structurally specific fragment ions. The method can provide both sensitivity and specificity for the Q3 MRM ions. In some embodiments, ionization can be sued to produce a dominant neutral loss fragment ion which can be selected in Q3 and then fragmented to produce structurally specific ions. These fragment ions can then be used for identification and quantification in a procedure referred to as MS3.

EXAMPLES

Aspects of the present invention may be further understood in light of the following examples, which are not exhaustive and which should not be construed as limiting the scope of the present teachings in any way.

Example 1

MALDI Analysis of Ketosteroids

Figure 2:
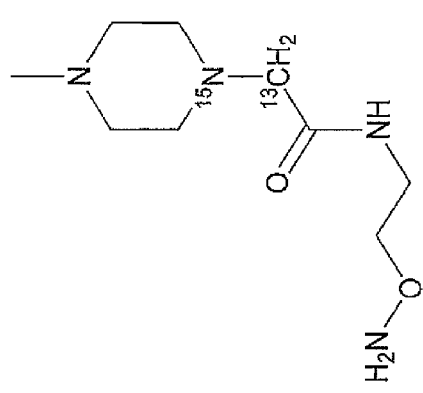
FIG. 2 shows four chemical structures of four mass differential reagents for derivatizing a ketone or aldehyde analyte.
Figure 2:
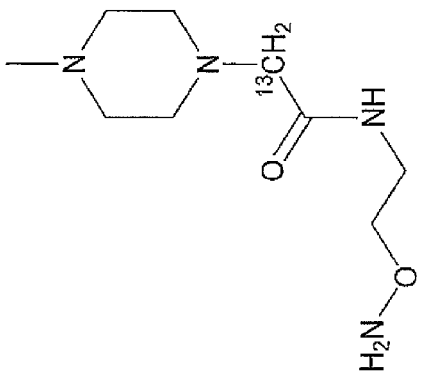
Figure 2:
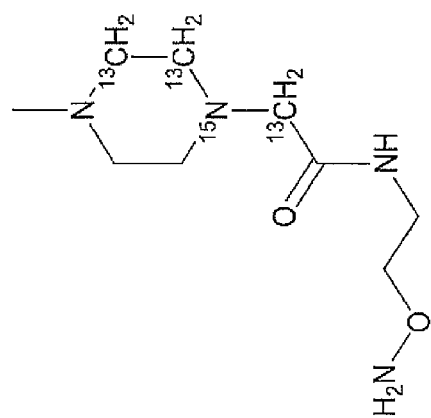
Figure 2:
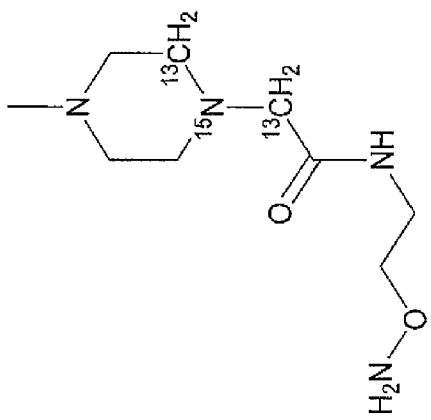
Figure 3A:
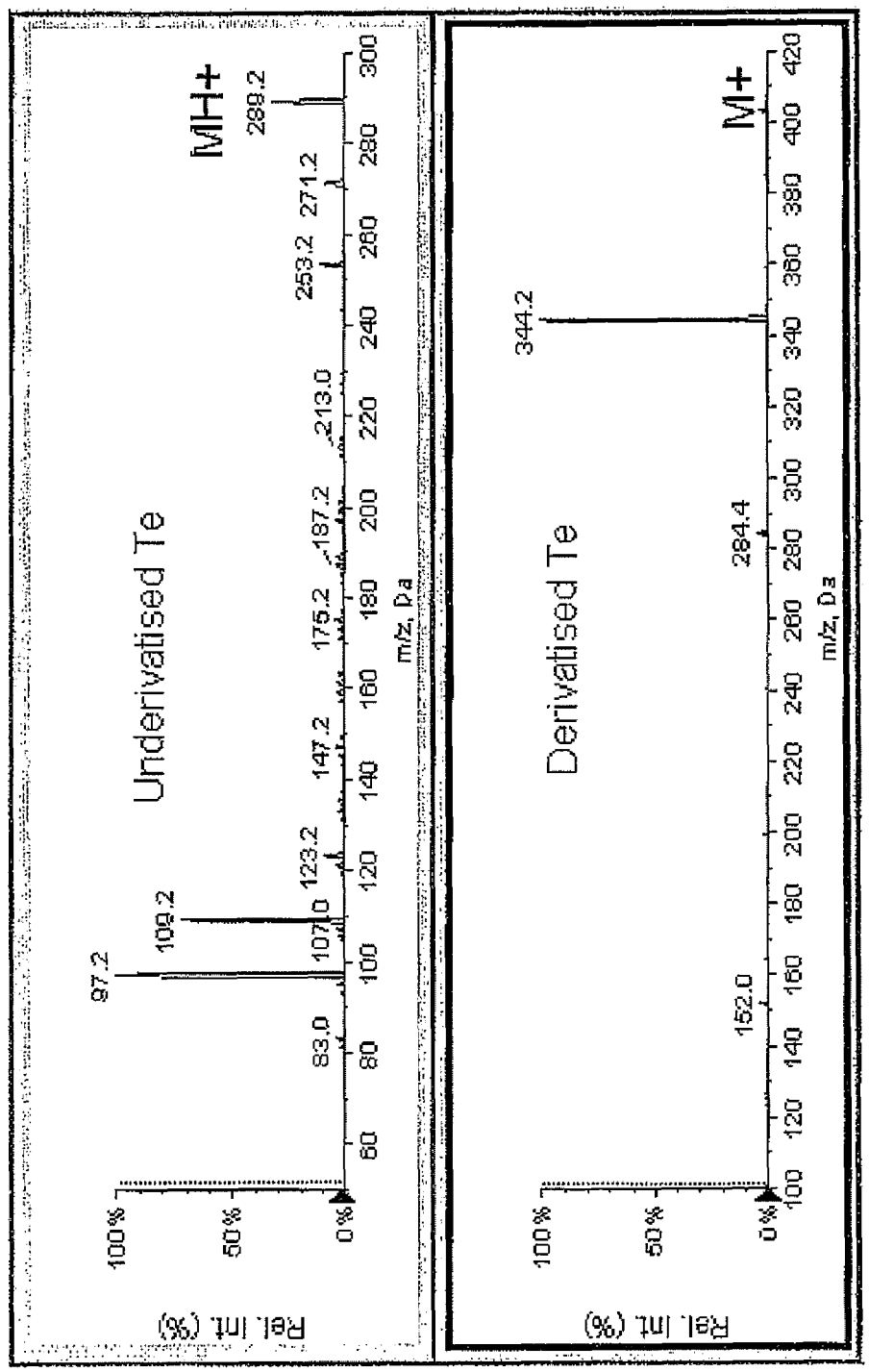
FIGS. 3A-3D are MS spectrum of derivatized and underivatized ketosteroid analytes: 3A is underivatized (top) and derivatized (bottom) testosterone; 3B is underivatized (top) and derivatized (bottom) progesterone; 3C is underivatized (top) and derivatized (bottom) pregnenolone; and 3D is underivatized (top) and derivatized (bottom) aldosterone.
Figure 3B:
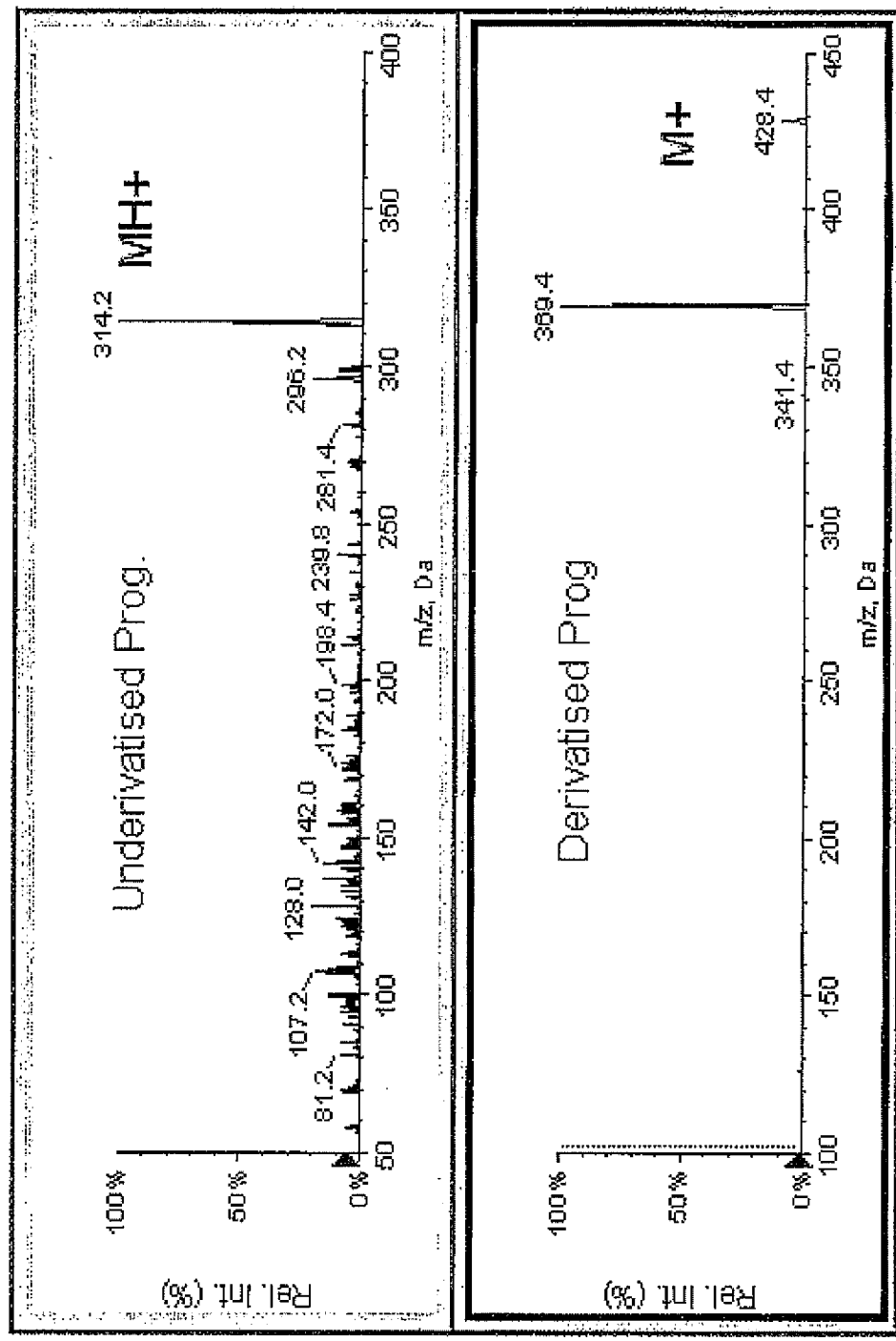
Figure 3C:
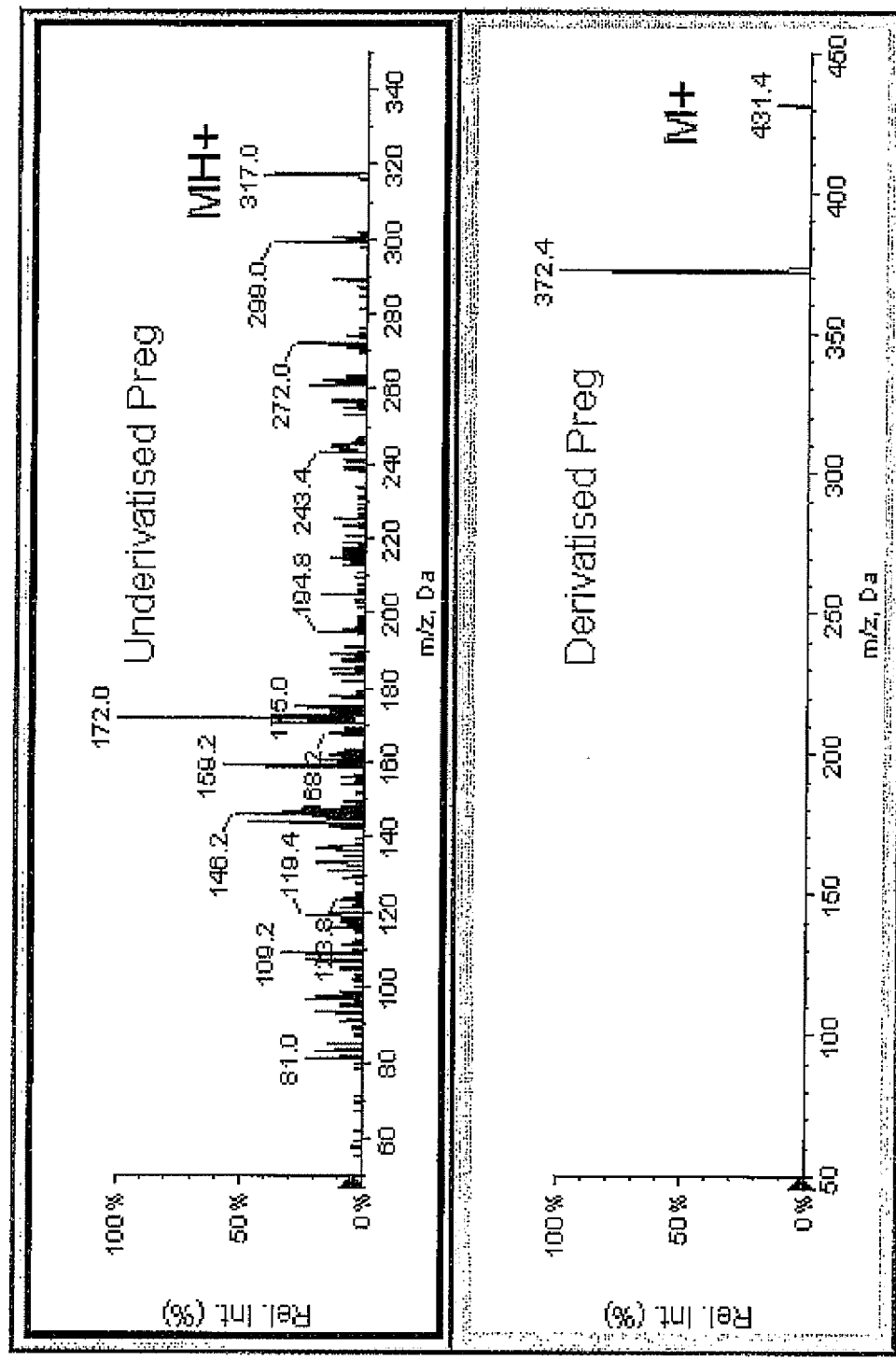
Figure 3D:
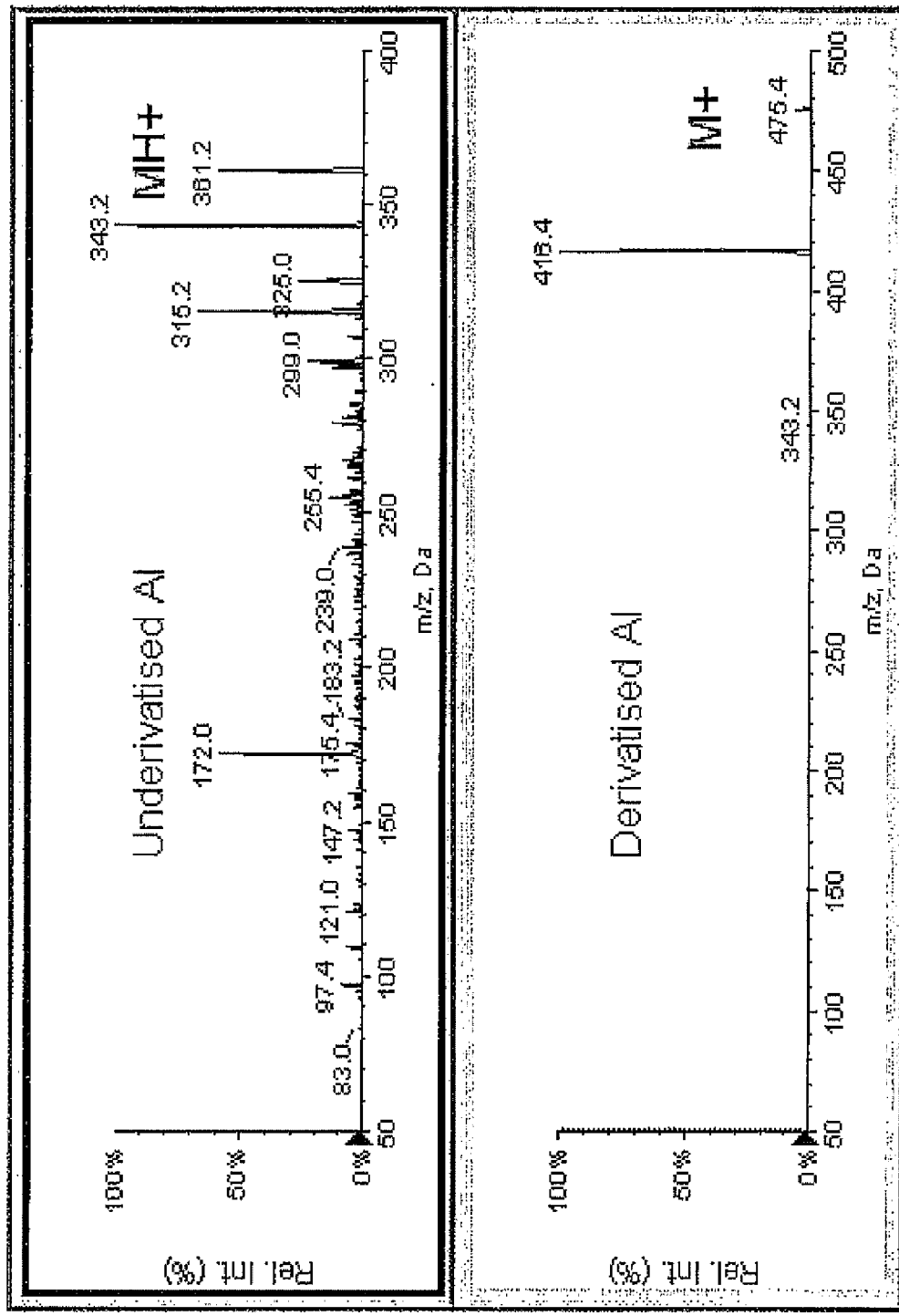

A representative synthesis of a labeling reagent, see FIG. 2, is performed as follows:

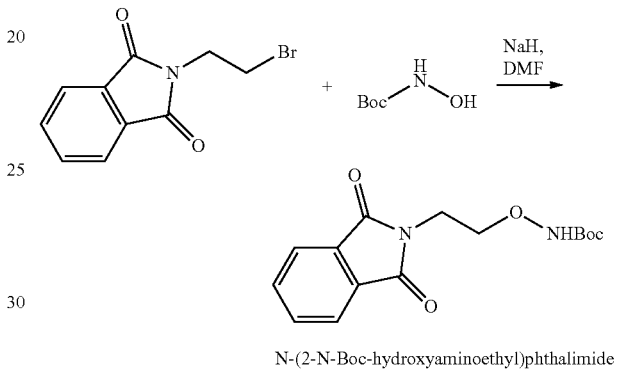

N-(2-N-Boc-hydroxyaminoethyl)phthalimide

N-(2-N-Boc-hydroxyaminoethyl)phthalimide: To a suspension of NaH (2.02 g, 50.56 mmol, 60% dispersion in oil) in DMF (25 mL) a solution of BocNHOH (6.12 g, 133.15 mmol) in DMF (25 mL) was added dropwise at ambient temperature from an addition funnel under nitrogen atmosphere. After completion of addition, the reaction mixture was heated to 55-60° C. for 20 min when a faint yellow color solution formed. A solution of N-(2-bromoethyl)phthalimide (7.79 g, 30.64 mmol) in DMF (50 mL) was then added dropwise to the reaction mixture over 20 min and the reaction continued at 55-60° C. for another 2 h. After removal of DMF under reduced pressure, the oil was partitioned between EtOAc (300 mL) and 0.5 M HCl (150 mL). EtOAc layer was washed with brine (50 mL), dried over $Na_2SO_4$, and concentrated to an oil. The oil was purified by flash chromatography (40-70% EtOAc in hexanes, 330 g silica column) to give 1.65 g (18%) of the desired product (N-(2-N-Boc-hydroxyaminoethyl)phthalimide $R_f$=0.42 in 30% EtOAc in Hexanes, silica plate; ES-MS, calculated $MH^+$=307.1. found 307.1).

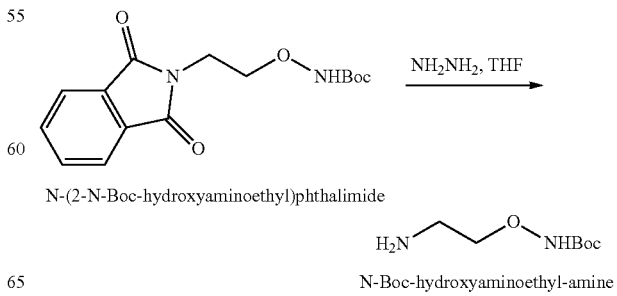

N-(2-N-Boc-hydroxyaminoethyl)phthalimide

N-Boc-hydroxyaminoethyl-amine

N-Boc-hydroxyaminoethyl-amine: N-(2-N-Boc-hydroxyaminoethyl)phthalimide (1.65 g, 5.38 mmol) was treated with $NH_2NH_2$ solution in THF (1 M, 25 mL, 25 mmol) at ambient temperature for 20 h. After removal of solvent and volatiles under well ventilated condition the solid residue was treated with 100 mL of dichloromethane, mixed well and filtered. The solid cake was washed twice with dichloromethane (25 mL). Combined dichloromethane filtrate was concentrated to a colorless oil. The oil was purified by flash chromatography (120 g silica column, 9:1:0.1 dichloromethane-MeOH-$Et_3N$). Fractions containing the product (ninhydrin stain) were combined and concentrate to give a white solid, which was portioned between 6 M NaOH (50 mL) and dichloromethane (200 mL). Dichloromethane layer was dried over $Na_2SO_4$ and concentrated to give the desired product N-Boc-hydroxyaminoethyl-amine as oil (0.29 g, 31%). ES-MS, calculated $MH^+$=177.2. found 177.2.

and treated with 4 M HCl in dioxane (3 ml) for 45 min. After evaporation of dioxane, the oil was triturated with dichloromethane to give pip-AO-117 and pip-AO-114 as white solids (66-70% yields). ES-MS, calculated $MH^+$=221.2. found 221.2. As will be readily appreciated by those skilled in the art, synthesis of reagents 115 and 116 and the non-isotopically enriched species 113 are produced by an analogous synthetic route.

Using MALDI—MRM instrumentation, highly selective quantitiation of small molecules can be performed at a rate of less than 5 seconds per sample, eliminating the background noise created by the MALDI matrix in the low mass range.

Referring to FIG. 1, the chemical structures and molecular weights certain ketosteroids are given. To determine the labeling compound and methods described herein, four representative steroids were chosen (FIG. 1) Testosterone (Te), Aldosterone (AL), Pregnenolone (Preg) and Progester-

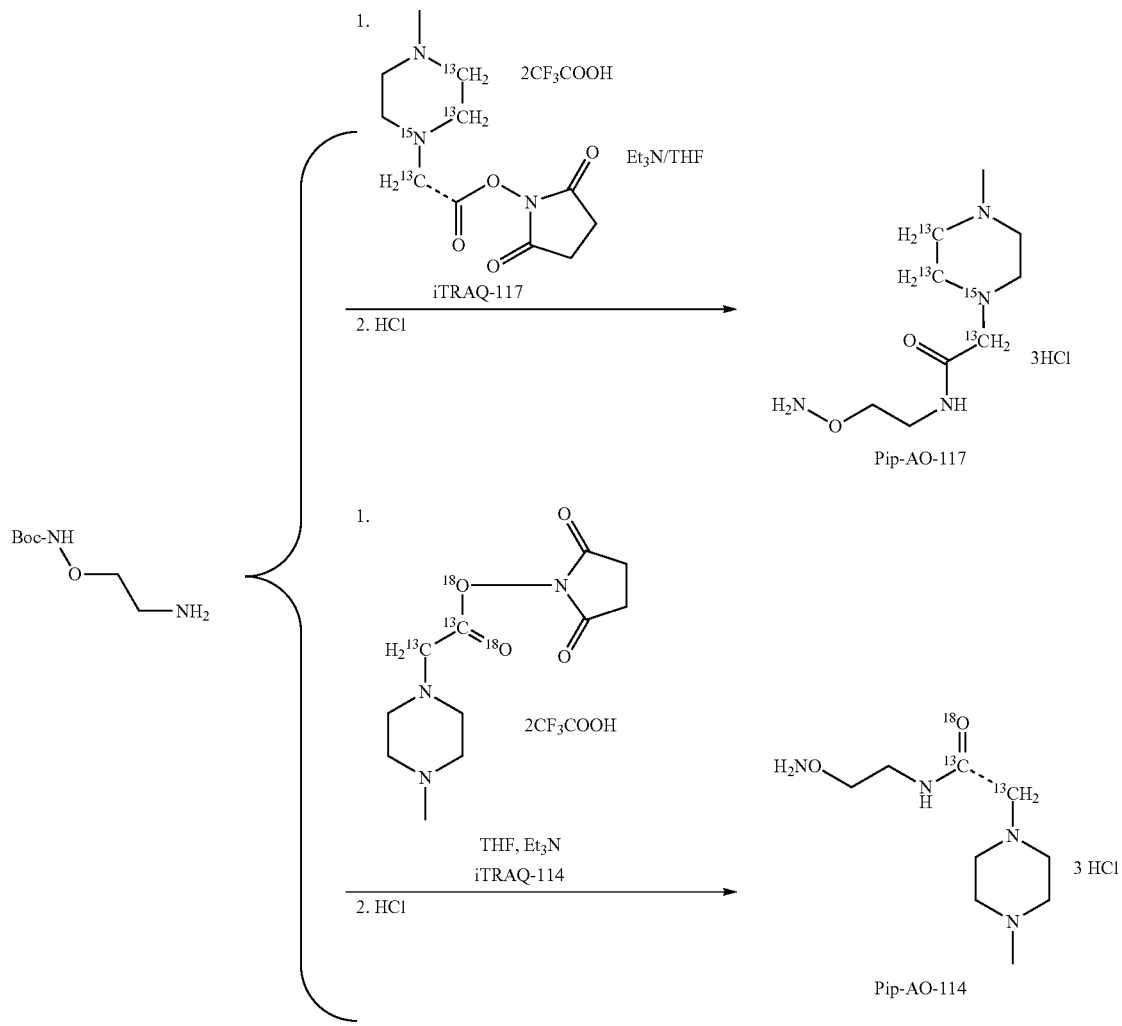

Pip-AO-117 and Pip-AO-114: To a solution of iTRAQ-114 and -117 reagents (0.73 mmol) in THF (1 mL) was added a solution of N-Boc-hydroxyaminoethyl-amine (0.57 mmol) in THF (2 mL) followed by $Et_3N$ (3.7 mmol), mixed, and heated at 50° C. for 1 h. TLC ($R_f$=0.7, 8.5:1:0.1 dichloromethane-MeOH-$Et_3N$. silica plates) showed formation of one product which was purified by flash chromatography (12 g Silica column, 9:1:0.1 dichloromethane-MeOH-$Et_3N$). Fractions containing pure product were concentrated one (Prog). Progesterone was used as an Internal Standard (IS). As noted above, the derivitization procedure relies on the animooxy (R) reaction with an aldehyde or ketone to yield to oxime (X) resulting in a labeled ketone or aldehyde compound.

Derivatization Procedure: A mixture of Te, AL and Preg (0.1 mg/mL each) was reacted with the reagent in MeOH+ 10% AcOH and incubated for 30 min at RT. The volume of the reaction was 100 µL and the ratio steroid:reagent was 1:500 eqv. Prog was derivatized separately under similar conditions. The derivatized steroids were diluted in ACN/H$_2$O before MALDI plate spotting. The steroid sample (S) is mixed with excess matrix (M) and dried on a MALDI plate. The plate is loaded onto the sample stage in the ion source. Laser beam produces matrix neutrals (M), matrix ions (MH)+, (MH)−, and sample neutrals (S). MALDI plate spotting: The steroid sample was mixed with the MALDI matrix α-cyano-4-hydroxycinnamic acid (CHCA) dissolved in ACN/H2O 1/1 V/V+0.1% TFA (10 mg/mL). 0.75 μL spotted on each well and air dried. MALDI Instrument and MRM conditions: Analysis was performed on a 4000 QTRAP® (ABI; Foster City, Calif.) with FlashLaser™ source which is a high repetition laser optimized for the analysis of small molecules. The compound dependent and MRM parameters are described in Table 1. Sample molecules are ionized by proton transfer from matrix ions: MH++S→M+SH+, MH−+S→X+SH−. The FlashLaser™ source, equipped with a high repetition laser, generates ultra fast signal from samples spotted on a target plate.

TABLE 1

MALDI-MRM Parameters

| Steroid | Laser Power, Plate Voltage | MRM Transition | CE (eV) | CXP |
|---|---|---|---|---|
| Testosterone (Te) | 15%, 70 V | 289→109 | 35 | 10 |
| Derivatized Te | 15%, 70 V | 403→344 | 30 | 9 |
| Aldosterone (AL) | 15%, 70 V | 361→325 | 27 | 16 |
| Derivatized AL | 15%, 70 V | 475→416 | 35 | 9 |
| Pregnenolone (Preg) | 15%, 70 V | 317→159 | 47 | 9 |
| Derivatized Preg | 15%, 70 V | 431→372 | 35 | 15 |
| Derivatized Prog (As Internal Standard) | 15%, 70 V | 428→369 | 35 | 10 |

FIG. 2 is the chemical structure of reagents designated 114, 115, 116 and 117 having the formula Z—R$_1$ where R$_1$ is the terminal aminoxy O—NH$_2$ described herein and Z is the mass reporter group.

Figure 4:
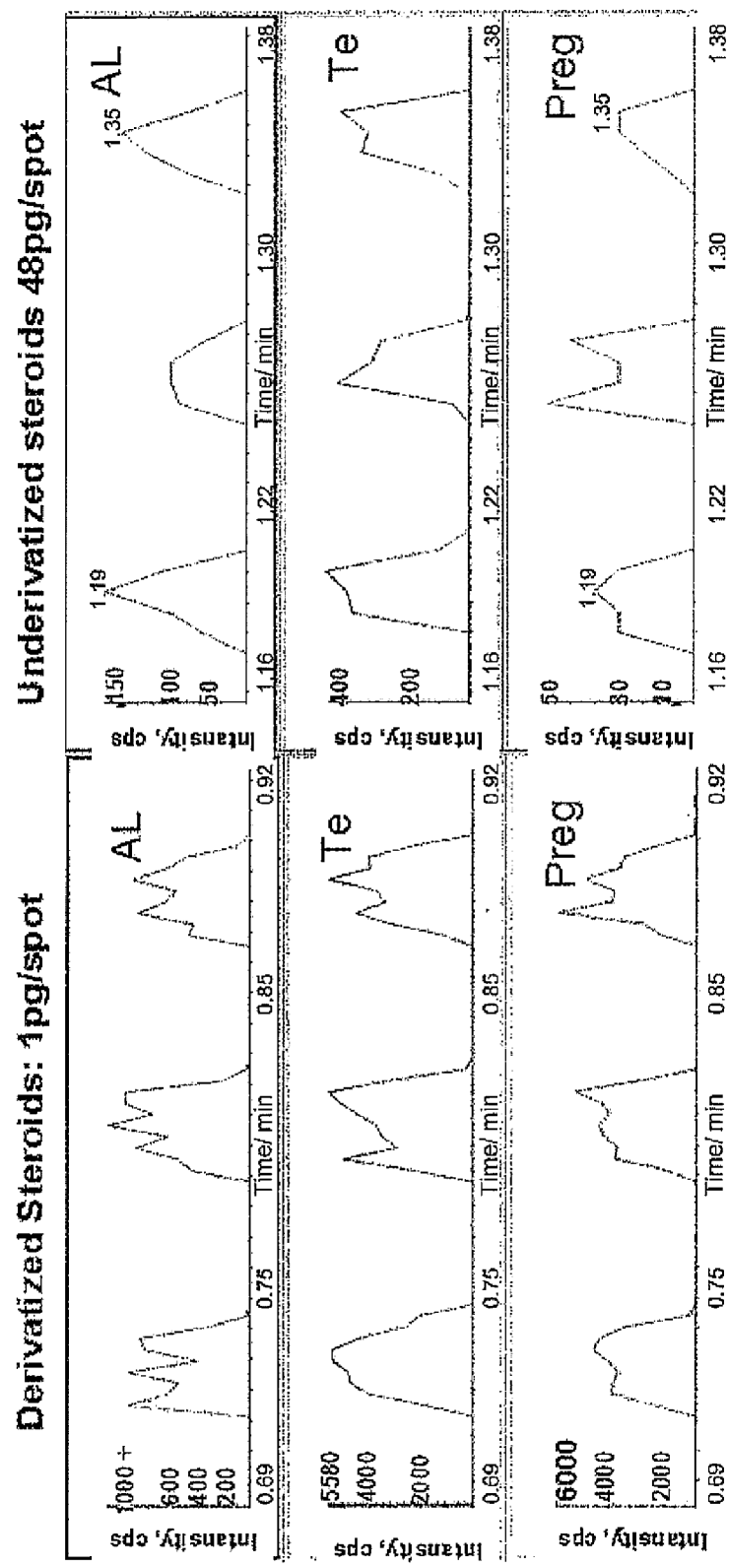
FIG. 4 is triplicate MALDI-MRM peaks for derivatized (1 pg/spot) and underivatized (48 pg/spot) aldosterone, testosterone, and pregnenolone.

FIGS. 3A-3D are product ion scans of underivatized and derivatized ketosteroids A: testosterone (CE=30 eV for both); B: Progesterone (CE=35 and 32 eV repectively); C: Pregnenolone (CE=40 and 35 eV respectively); and D: Aldosterone (CE=35 eV for both). A comparison of the spectra of derivatized and underivitized ketone compounds in each of FIGS. 3A, 3B, 3C, and 3D shows the increase in sensitivity and specificity achieved under high throughput conditions. Similarly, FIG. 4 shows triplicate MALDI-MRM peaks for derivatized and underivatized aldosterone, testosterone and pregnenolone measured for the labeling and analytical methods and strategies described herein.

Figure 5:
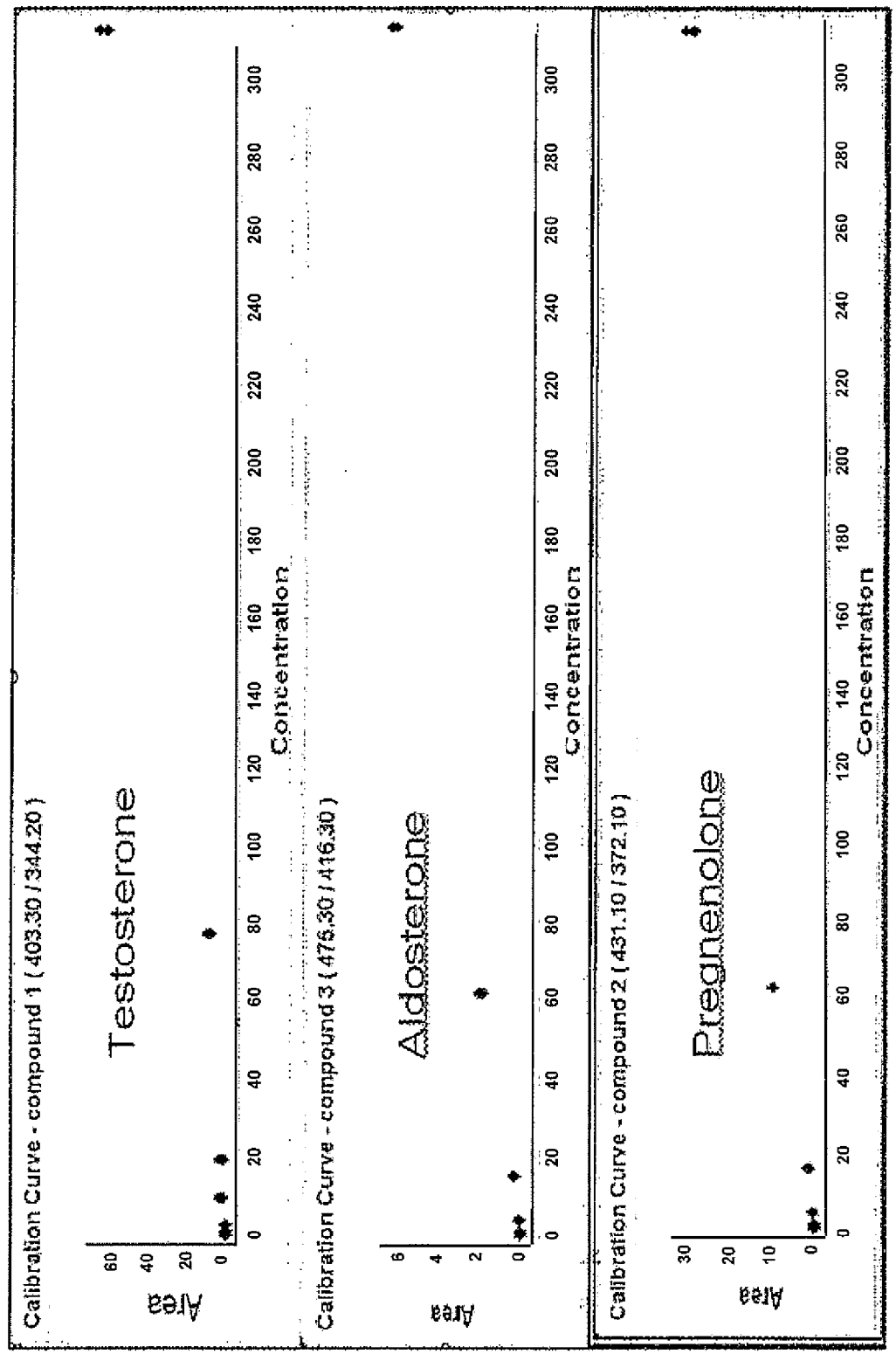
FIG. 5 is concentration calibration curves for testosterone, aldosterone, and pregnenolone.

FIG. 5 shows concentration calibration curves for testosterone, aldosterone and pregnenolone at 0.07-312 pg/spot generated for mass analysis of the species described above.

TABLE 2

LOD values and Signal enhancement factor s of Te, AL and Preg

| Ketosteroid | LOD Underivatized pg/spot | LOD Derivatized pg/spot | MRM Signal Enhancement Factor |
|---|---|---|---|
| Testosterone | 4.8 | 0.007 | 700 |
| Aldosterone | 12.8 | 0.04 | 320 |
| Pregnenolone | 45 | 0.007 | 6428 |

Derivatization of neutral ketosteroids have proven to enhance significantly their MALDI-MRM sensitivity. Referring to FIGS. 3A-3D and 4, the improved ionization efficiency resulted in simplified MS/MS fragmentation as the precursor ion is converted to only one major product. The combination of instrumental innovation (high repetition laser for MALDI-MRM) with chemistry (introduction of an easily ionizable moiety) resulted in a powerful high throughput, high sensitivity, and high specificity method for steroids analysis. The ketosteroids investigated in this study could be detected simultaneously in low fg/spot concentrations within <5 seconds. Concentration curves resulted in R2>0.99 over >3 orders of magnitude. MALDI spotting and sample clean up is easily be automated for routine clinical screening and target analysis.

Example 2

Derivatization of Ketosteroids and Detection Via LC-MS

Figure 6:
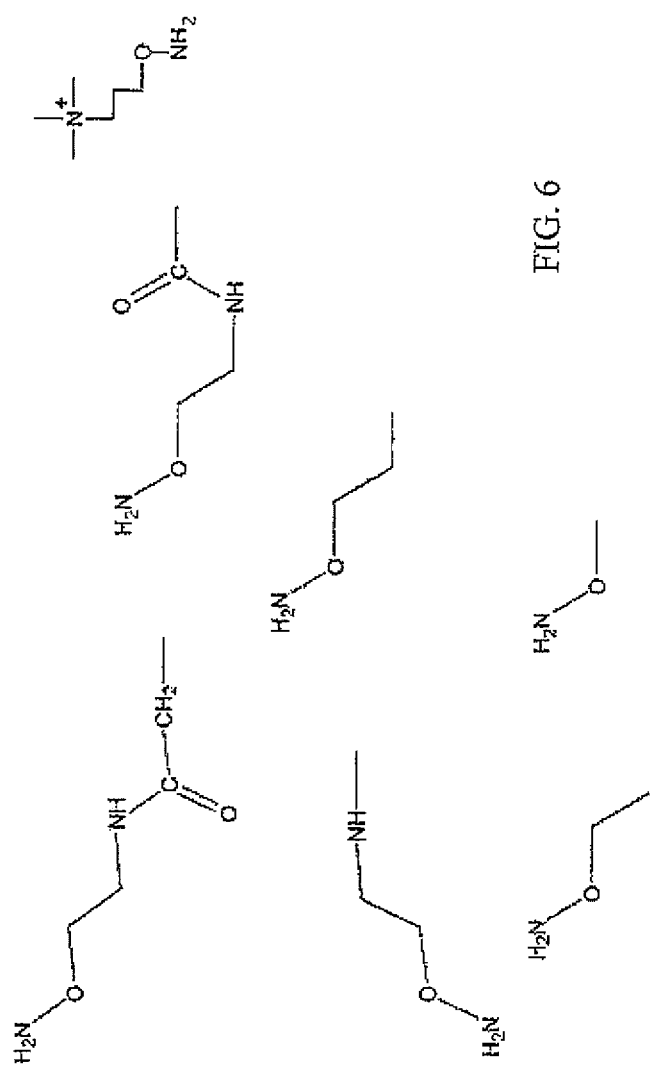
FIG. 6 is chemical structures of suitable terminal aminoxy groups suitable for the labeling reagents disclosed herein and a quarternary amino mass balance moiety also comprised at a terminal aminoxy functionality.
Figure 7:
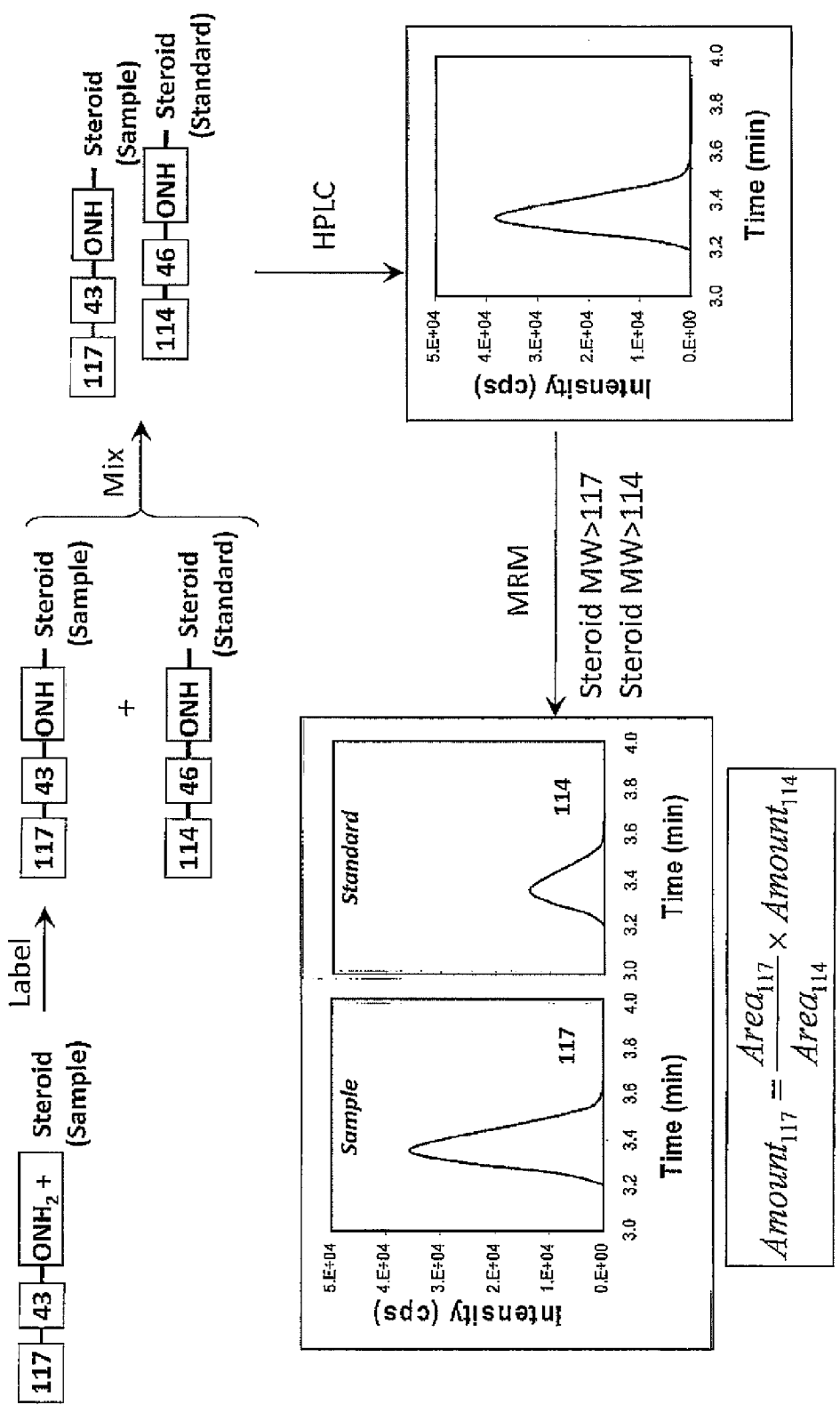
FIG. 7 is an outline of an analytical strategy and workflow method for derivatizing, analyzing, and calculating the concentration of a ketone or aldehyde compound using the techniques described herein.

As noted above, the ketone group of a ketosteroid is derivatized to an oxime functional group (X) by reaction with the label of the formula Z—R$_1$. Exclusively protonated molecular ions are formed without sodium (Na) or potassium (K) additives. Fragmentation of the derivatized ketosteroid analyte yields a simplified spectrum with a dominant signature ion at 117 Da generated from the reporter group. Referring to FIG. 7, the derivatization procedure described herein takes advantage of the use of a heavy version as an internal standard for quantitation. FIG. 7 is a simple flow chart for the quantitative analysis of a steroid comprising a ketone or aldehyde group as described herein. Initially, the analyte and a standard are derivatized by aminoxy chemistry followed by mixing the labeled analyte and sample. The mixture is subjected to chromatographic separation, for example, by LC such as by HPLC, followed by mass analysis by MRM. Quantitation is enabled by relative or absolute measurement of the signal derived from one or more analytes and standards. Also, Z may comprise a mass balance group, such as the quarternary amine shown in FIG. 6, and the positive charge is transferred to the analyte which functions as the reporter group to be detected by mass spectrometry. R$_1$ remains the terminal aminoxy moiety.

According to various embodiments, the aminoxy MS tagging reagents can be used for relative and absolute quantification in multiplex assays. According to some embodiments, the aminoxy MS tagging reagents can be used for two-plex, three-plex, four-plex, and other multi-plex assays. An exemplary method of quantification is shown with reference to FIG. 7, which illustrates absolute quantification for a two-plex assay. As described in FIG. 7, the method can begin with labeling a first sample containing a known analyte, in this case, a steroid. The first sample can be, for example, a standard containing a known concentration of a known steroid. The first sample can be labeled with a first aminoxy tag from a set of aminoxy tags. Next, a second sample having an unknown steroid in an unknown concentration can be labeled with a second aminoxy tag from the same set of aminoxy tags. The labeled first sample can then be combined with the labeled second sample to form a mixture.

Subsequent to mixing, the mixture can be subjected to separation, such as high performance liquid chromatography (HPLC) separation, or liquid chromatographic separation on a reversed phase column. The labeled steroids can elute from the column at separate times due to their different and distinct retention times on the column. The peaks eluted from the reversed phase column comprise peaks that contain the labeled steroids from the first sample and peaks that contain the labeled steroids from the second sample. Next, each peak eluted from the column can be subjected to Parent Daughter Ion Transition Monitoring (PDITM). The ratio of the signal intensity of peak area of the reporter signals generated from the first sample, relative to those generated from the second sample, gives the relative concentration of the steroid in the test sample. When the concentration of the labeled standard is known, the specific concentration of the analyte in the sample can be determined, as shown in FIG. 7.

A panel of 8 ketosteroids comprised of derivatized and underivatized testosterone, progesterone, epi-androsterone, pregnenolone and prednisolone was subjected to LC-MS analysis using a reverse phase C8 column (Luna C8, 5 nM, phenomenex) and a water/formic acid gradient over 10 minutes. Mass analysis used an API 4000 QTRAP in MRM mode. Derivatization was 10% acetic acid in MeOH at room temperature for 30 minutes.

Figure 8A:
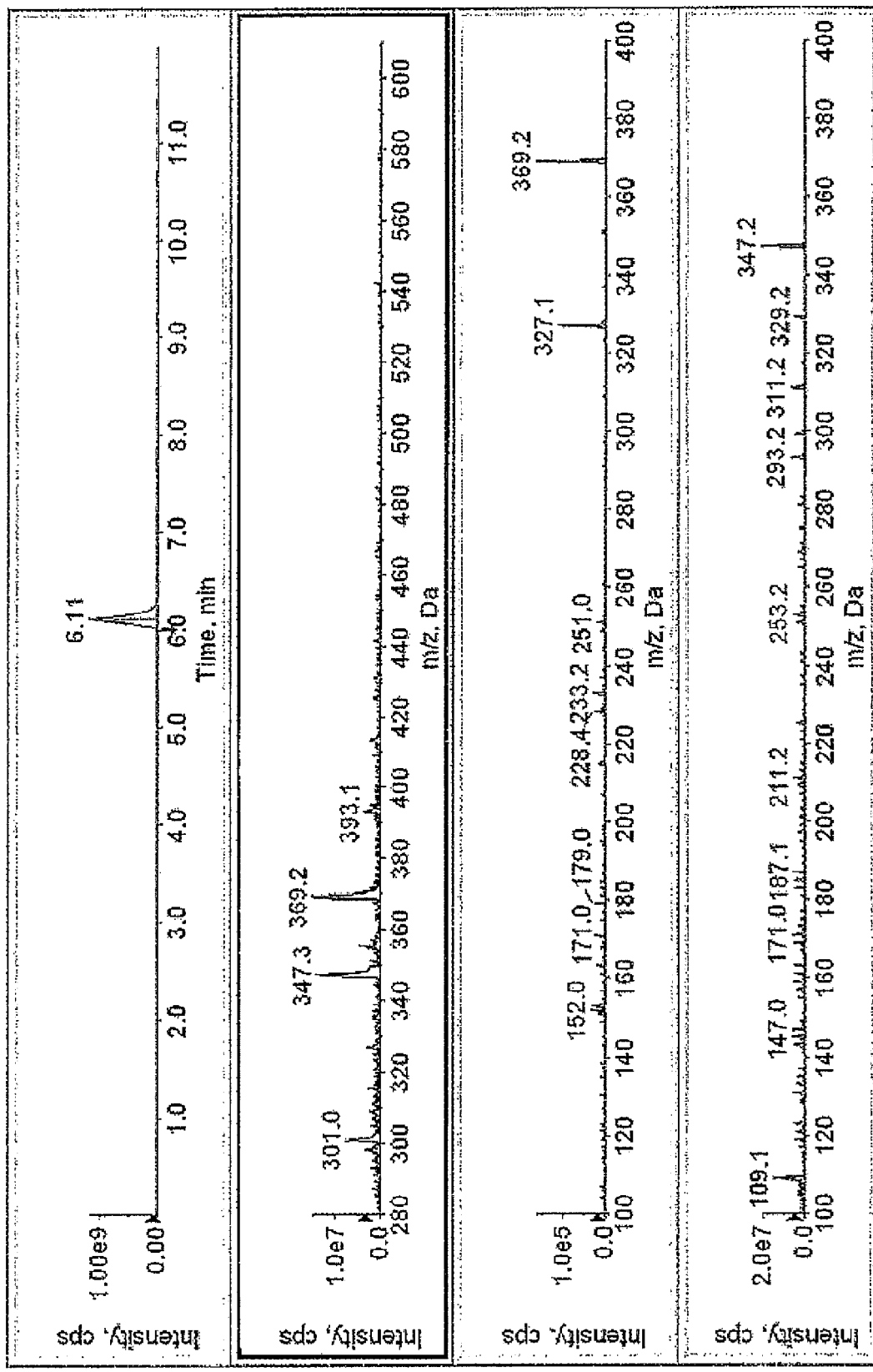
FIGS. 8A-8B are MS spectra of underivatized (8A) and derivatized (8B) cortexolone.
Figure 8B:
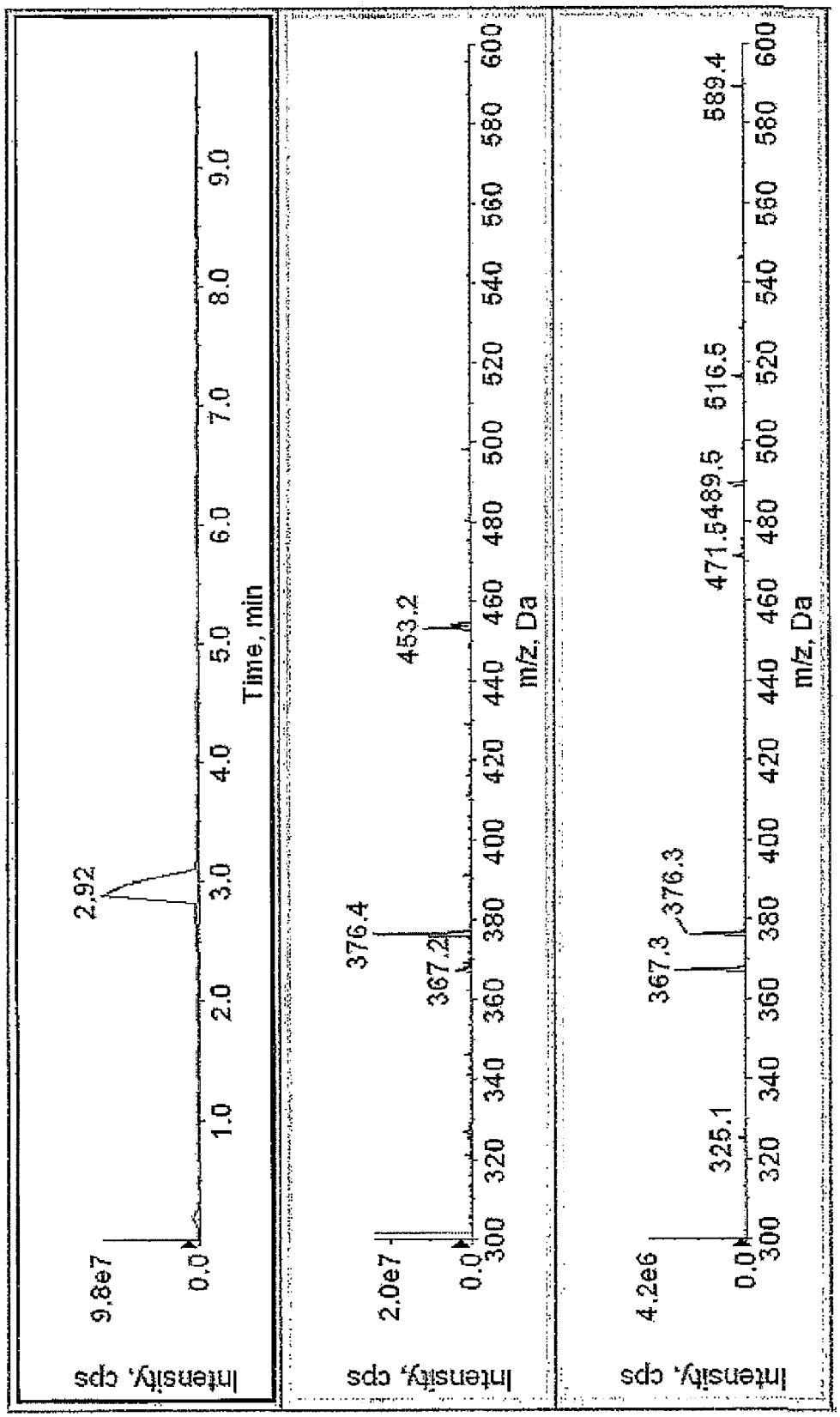

Referring to FIGS. 8A-8B, underivatized ketosteroids tend to distribute the ion current between several species. An example of cortexolone is shown (FIG. 8A) where strong Na+ adducts are observed. Product ion spectra of ketosteroids generated very complex fragmentation patterns, both the [M+H]+ and [M+Na]+ of underivatized Cortexolone produced fragment ions distributed across the entire spectra (FIGS. 8A & 8B).

Referring to FIG. 8B, in contrast, LC-MS analysis of derivatized ketosteroids produced strong [M+H]+ with little Na or K adducts (FIG. 3). Product ion spectra were simplified with a strong signature from the derivatized analyte at 117 Da. Fragmentation from the steroid backbone was still present but represented a mere few percent of the ion current.

Figure 9:
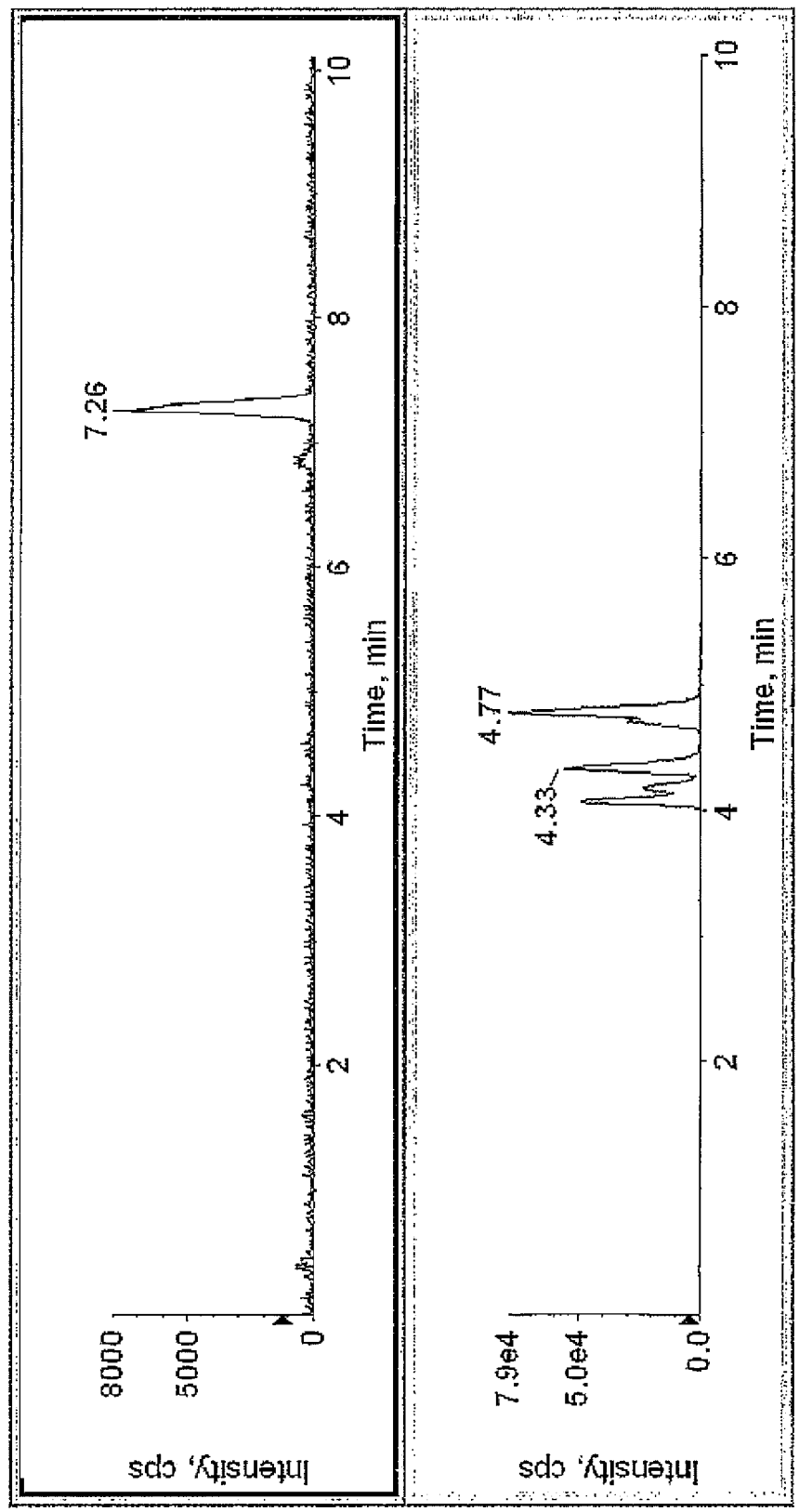
FIG. 9 is an MALDI analysis of 1 pg of testosterone/epitestosterone in derivatized (a) and underivatized (b) forms.

Similarly, FIG. 9 shows an MRM analysis of 1 pg of testosterone/epi-testosterone in derivatized (a) and underivatized (b) forms. Sensitivity improvement from the derivatization procedure is shown for testosterone and epi testosterone. 1 pg of derivatized testosterone produced a 10× increase in sensitivity compared to underivatized testosterone. A peak shoulder is observed for derivatized due to separation of the cis/trans isomer created from the derivatization procedure. The peak at 3.96 mins is dehydro-epi-androsterone which was also presented in the derivatization mix.

Figure 10:
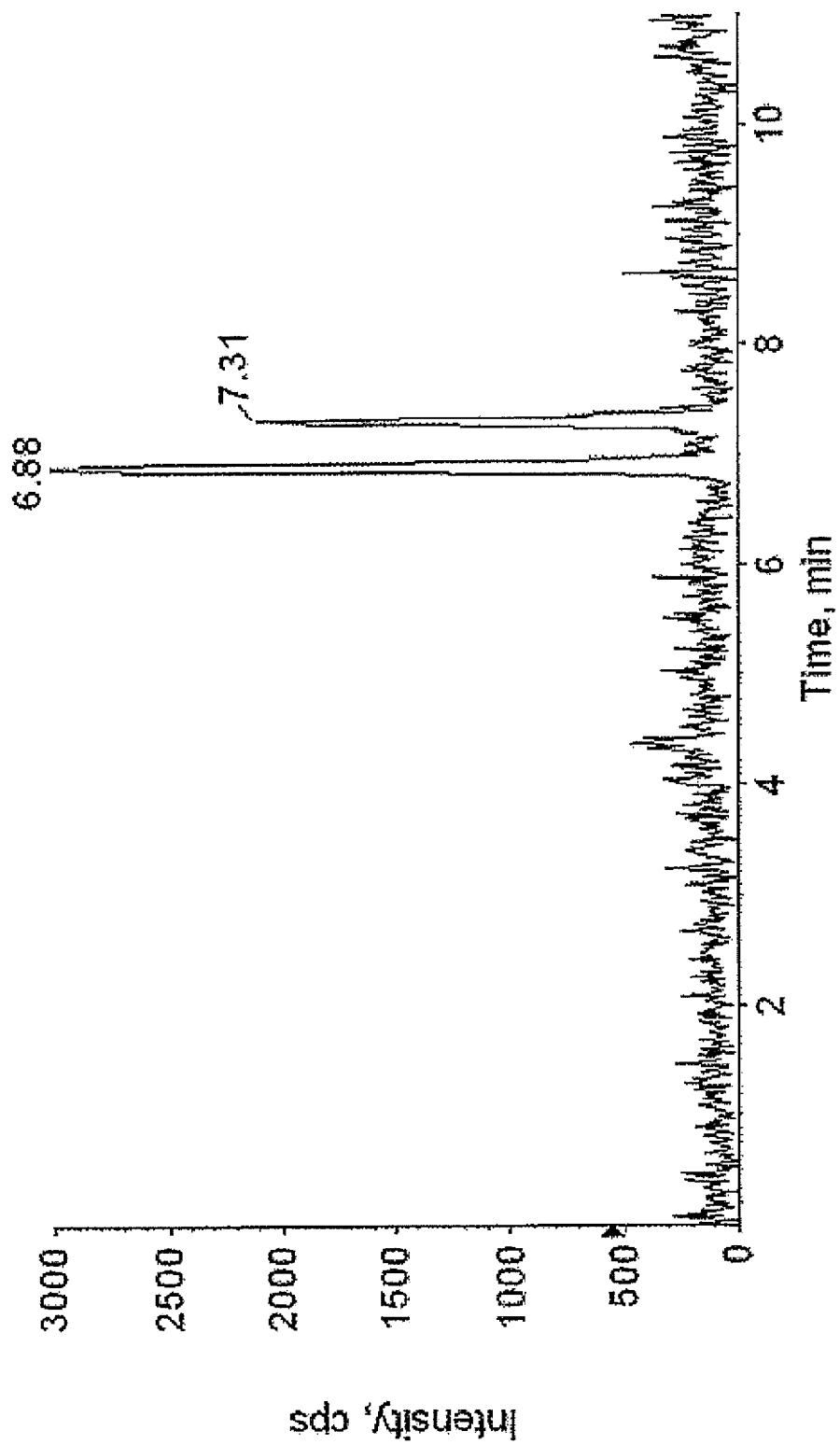
FIG. 10 is a graph of reaction efficiency calculated to be >99%.

FIG. 10 shows the reaction efficiency. Reaction efficiency was evaluated by injecting 300 pg of derivatized testosterone and epi testosterone and measuring the amount of underivatized analyte. Reaction efficiency was calculated to be >99%.

Figure 11:
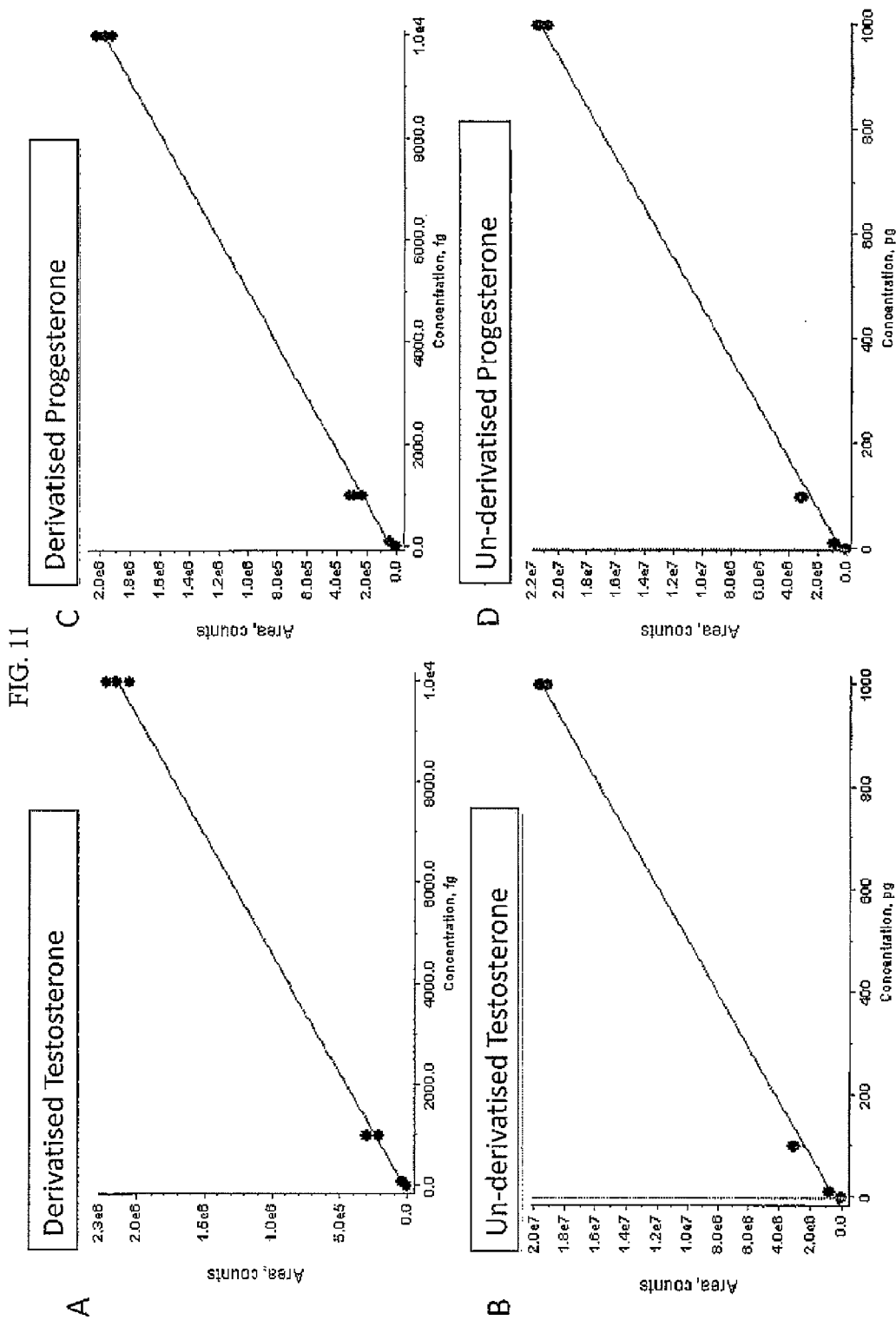
FIG. 11 shows the reaction quantitation of the aminoxy chemical derivatization in a calibration curve generated from a serial dilution of derivatized and underivatized testosterone.

FIG. 11 shows the reaction quantitation. To test quantitation of the aminoxy reaction, a dilution series (10 fg-10000 fg) and derivatized sample were analyzed. The resultant calibration curve was linear and compared well to a dilution series of the underivatized form of the sample (10 fg-10000 fg).

TABLE 3

Comparison data for derivatized ketosteroids

| Ketosteroid | LOQ Underivatized (fg) | LOQ Derivatized (fg) | LOQ Derivatized Analyzed in PPP |
|---|---|---|---|
| Cortexolone | 100 | 10 | 10 |
| Corticosterone | 100 | 10 | <10 |
| 17-alpha-hydroxy-progesterone | 100 | 1 | 10 |
| Progesterone | 100 | 1 | 10 |
| Pregnenolone | 10000 | 10 | 10 |
| Prednisolone | 200 | 10 | 10 |
| Epitestosterone | 1000 | 1 | 10 |
| Testosterone | 100 | 1 | 10 |

The data shown in the FIGS. and accompanying text show that the derivatization of ketone compounds using a label of the formula Z—$R_1$ using the aminoxy moiety to yield the oxime generated increases insensitivity by 10-1000 fold depending on the ketone compound, in this case the representative ketosteroid. The signature ion at 113 Da can be used as the Q3 mass for MS/MS.

Example 3

Derivatization of Ketosteroids Using Permanently Charged Aminoxy Reagent

Figure 12:
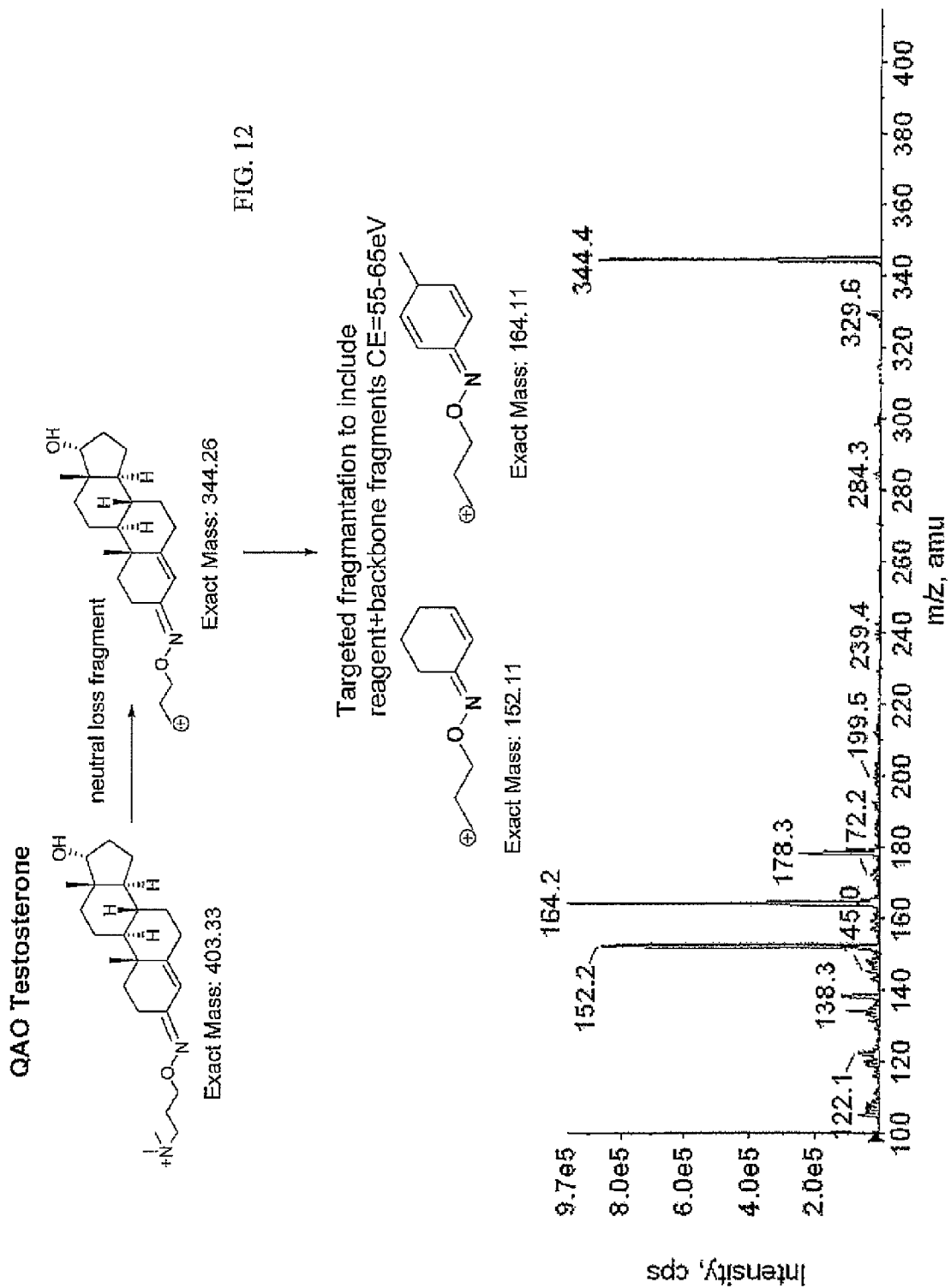
FIG. 12 shows the MS/MS fragments and spectrum of QAO Testosterone using CE=62 eV at which the signature ions contain fragments from both testosterone structure and from the derivatizing reagent structure, according to various embodiments of the present teachings.

FIG. 12 shows the MS/MS fragments and spectrum of QAO Testosterone using CE=62 eV at which the signature ions contain fragments from both testosterone structure and from the derivatizing reagent structure, according to various embodiments of the present teachings.

Figure 13:
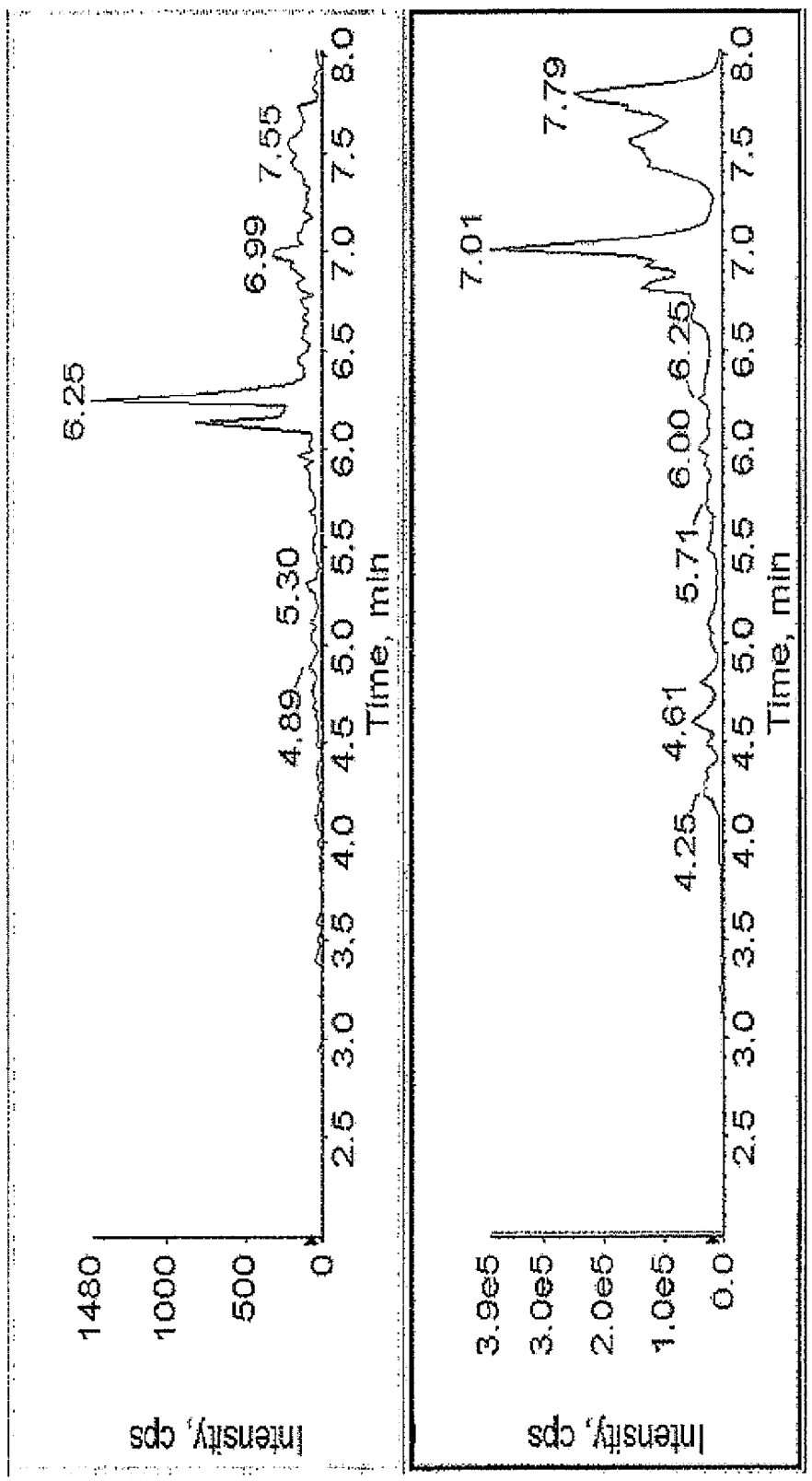
FIG. 13 shows the chromatograms of QAO derivatized testosterone using and MRM transition of a targeted Q3 fragment as compared to neutral loss Q3 fragment, according to various embodiments of the present teachings.

FIG. 13 shows the chromatograms of QAO derivatized testosterone using an MRM transition of a targeted Q3 fragment as compared to neutral loss Q3 fragment, according to various embodiments of the present teachings. Measurement involved using MRM transitions of neutral loss (403->344) vs. the reagent-plus-backbone fragment (304->162). As can be seen, lower detection limits are achievable using a Q3 transition that includes the reagent and the testosterone backbone, due to a significant reduction in background noise.

Figure 14:
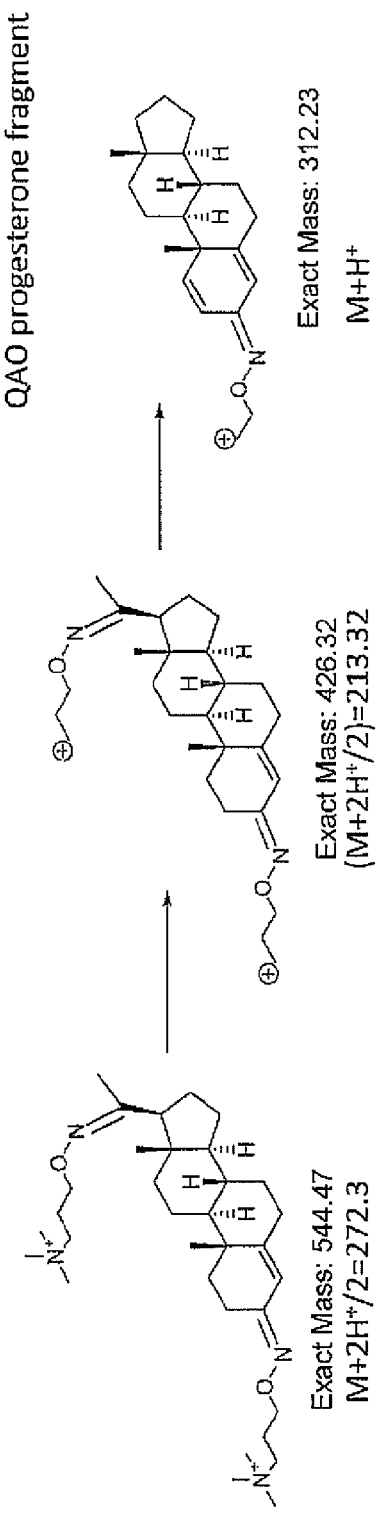
FIG. 14 shows the targeted MS/MS fragmentation and spectrum of QAO Progesterone and the MS/MS spectrum of QAO Testosterone at CE=62 eV.
Figure 14:
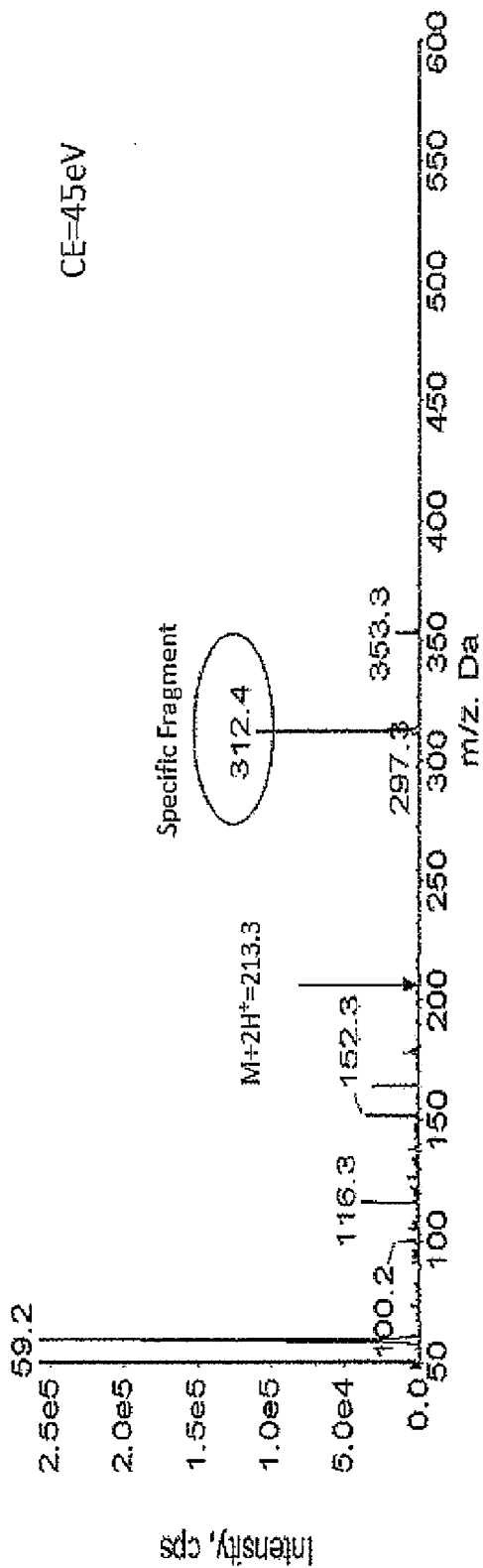

According to various embodiments of the present teachings, the method is applied to the targeted fragmentation of a ketosteroid. For example, FIG. 14 shows the targeted MS/MS fragmentation and spectrum of QAO Progesterone and the MS/MS spectrum of QAO Testosterone at CE=62 eV. QAO progesterone possesses two keto functionalities and therefore results in bis QAO progesterone.

Figure 15:
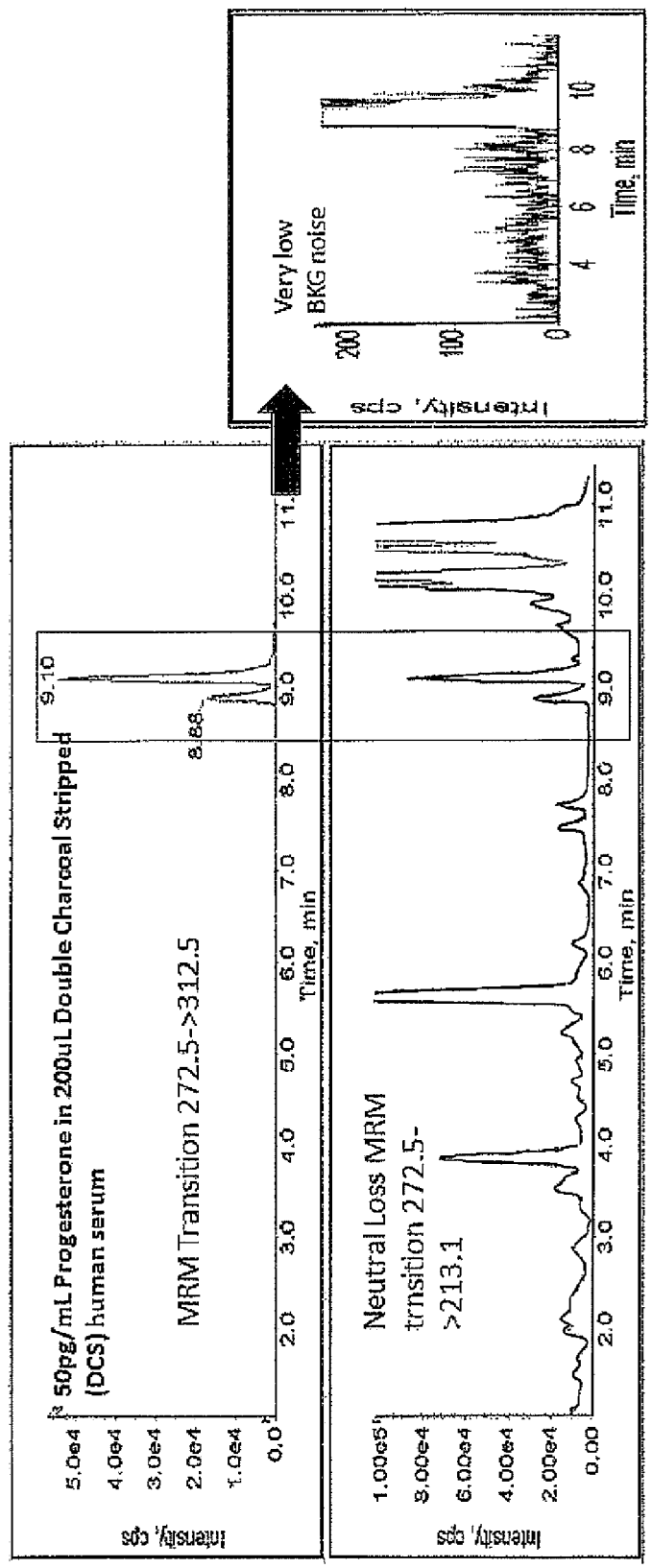
FIG. 15 shows the MS/MS spectrum of progesterone at CE=45 eV and illustrates a background noise reduction in an LC-MS/MS analysis.

FIG. 15 shows the MS/MS spectrum of progesterone at CE=45 eV. FIG. 15 illustrates the background noise reduction in an actual LC-MS/MS analysis. The MRM transition 272->213 is the neutral loss from the bis QAO progesterone doubly charged species, and a high background noise is noticeable. The MRM transition of 272->312.5 is the transition from the doubly charged bis QAO to a specific fragment that contains part of the reagent structure and part of the progesterone structure. This MRM transition from a lower Q1 mass to higher Q3 mass is even more specific and further improves specificity and reduces background noise in LC-MRM experiments.

Example 4

Sets of Tagging Reagents

The following is an exemplary set of four N-methylpiperazine-aminoxy mass differential reagents, according to various embodiments of the present teachings:

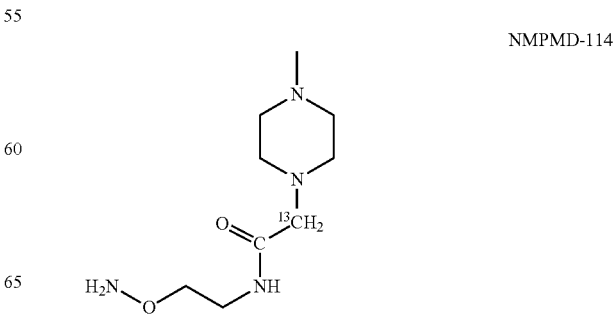

NMPMD-114

NMPMD-115

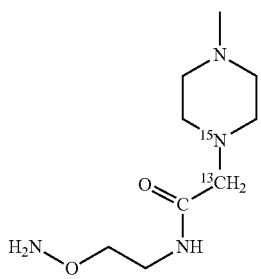

NMPMD-116

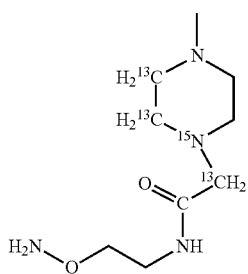

NMPMD-117

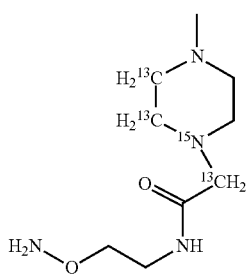

The following is an exemplary set of N-methylpiperazine-aminoxy isobaric reagents, according to various embodiments of the present teachings:

NMPIB-114

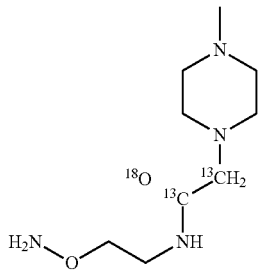

NMPIB-115

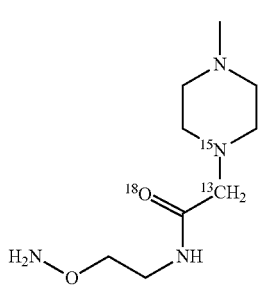

NMPIB-116

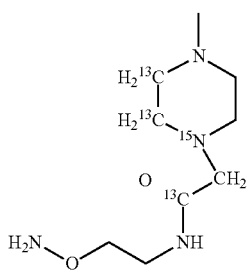

NMPIB-117

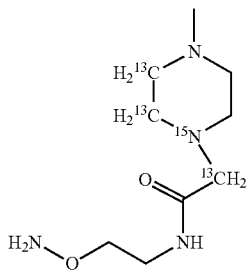

The following is an exemplary set of quarternary-aminoxy mass differential reagents, according to various embodiments of the present teachings:

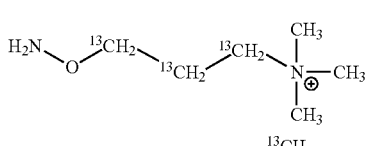

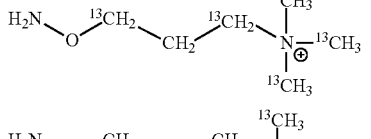

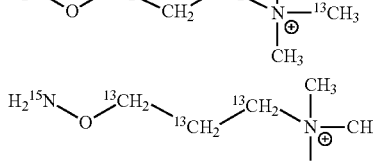

The following is an exemplary set of quarternary-aminoxy isobaric reagents, according to various embodiments of the present teachings:

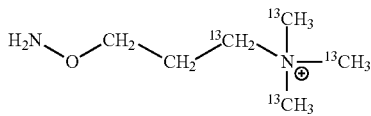

QAO + 1

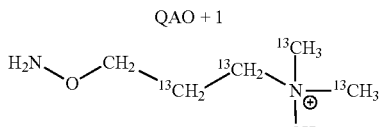

QAO + 2

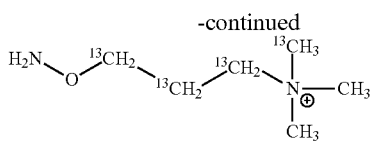

QAO + 2

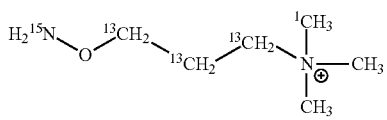

QAO + 4

All literature and similar material cited in this application, including, but not limited to, patents, patent applications, articles, books, treatises, and web pages, regardless of the format of such literature and similar materials, are expressly incorporated by reference in their entireties for all purposes. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

The teachings should not be read as limited to the described order or elements unless stated to that effect. It should be understood that various changes in form and detail may be made without departing from the scope of the present teachings. By way of example, any of the disclosed method steps can be combined with any of the other disclosed steps to provide a method of analyzing ring-containing compounds in accordance with various embodiments of the present teachings. Therefore, all embodiments that come within the scope and spirit of the present teachings and equivalents thereto are claimed.

The invention claimed is:

1. A method for mass analysis of an analyte in a sample comprising:
derivatizing an analyte comprising an aldehyde or ketone functional group, with a labeling reagent of formula:

Y—(CH$_2$)$n$-ONH$_2$ wherein n is an integer from 2 to 10 and Y is a group selected from the group consisting of:

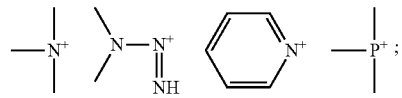

subjecting the labeled analyte to ionization; and
detecting the analyte by mass analysis.

2. The method of claim 1, further comprising determining a concentration of the analyte in a sample.

3. The method of claim 1, further comprising the step of subjecting the labeled analyte to ion fragmentation to yield an ionized reporter group.

4. The method of claim 1, wherein the step of detecting the analyte is comprised of detecting a first transmitted parent ion and a daughter ion fragment by parent-daughter ion transition monitoring.

5. The method of claim 1, wherein the labeling reagent contains one more heavy atom isotopes, the method further comprising derivatizing an aldehyde or ketone functional group of a standard compound with a labeling compound that is isobaric to the labeling compound used to form the labeled analyte and measuring the relative concentration of the analyte.

6. The method of claim 1, wherein the labeling reagent is isotopically enriched with two or more heavy atoms.

7. The method of claim 1, wherein at least two analyte compounds are derivatized with the labeling reagent and the method further comprises the step of determining a relative concentration between at least two analytes.

8. The method of claim 1, wherein at least two analyte compounds are derivatized with the labeling reagent and the method further comprises the step of determining an absolute concentration of at least one analyte.

9. The method of claim 1, wherein the ionization produces structurally specific fragment ions and Q3 MRM ions, the labeling reagent is wholly or partly contained in the structurally specific fragment ions, and the method provides both sensitivity and specificity for the Q3 MRM ions.

* * * * *